US012578346B2

(12) United States Patent
    Serie et al.

(10) Patent No.: US 12,578,346 B2
(45) Date of Patent: Mar. 17, 2026

(54) SYSTEMS AND METHODS FOR GLYCOPEPTIDE CONCENTRATION DETERMINATION, NORMALIZED ABUNDANCE DETERMINATION, AND LC/MS RUN SAMPLE PREPARATION

(71) Applicant: VENN BIOSCIENCES CORPORATION, South San Francisco, CA (US)

(72) Inventors: Daniel Serie, San Mateo, CA (US); Gege Xu, Redwood City, CA (US)

(73) Assignee: VENN BIOSCIENCES CORPORATION, South San Francisco, CA (US)

( * ) Notice: Subject to any disclaimer, the term of this patent is extended or adjusted under 35 U.S.C. 154(b) by 594 days.

(21) Appl. No.: 17/937,170

(22) Filed: Sep. 30, 2022

(65) Prior Publication Data

US 2023/0104536 A1     Apr. 6, 2023

Related U.S. Application Data

(60) Provisional application No. 63/293,506, filed on Dec. 23, 2021, provisional application No. 63/251,028, filed on Sep. 30, 2021.

(51) Int. Cl.
    *G01N 33/68*          (2006.01)

(52) U.S. Cl.
    CPC ..... *G01N 33/6848* (2013.01); *G01N 2496/80* (2013.01); *G01N 2570/00* (2013.01)

(58) Field of Classification Search
    None
    See application file for complete search history.

(56) References Cited

U.S. PATENT DOCUMENTS

| | | | |
|---|---|---|---|
| 9,746,464 | B2 | 8/2017 | Anderson |
| 10,352,942 | B2 | 7/2019 | Grote et al. |
| 2007/0269895 | A1 | 11/2007 | Aebersold et al. |
| 2016/0003842 | A1 | 1/2016 | Lee et al. |
| 2016/0168618 | A1 | 6/2016 | Kim et al. |
| 2020/0240996 | A1 | 7/2020 | Danan-leon et al. |

(Continued)

FOREIGN PATENT DOCUMENTS

EP          3 770 269  A1      1/2021

OTHER PUBLICATIONS

International Search Report and Written Opinion issued in corresponding International application PCT/US2022/077354 mailed Feb. 16, 2023.

(Continued)

*Primary Examiner* — Xiaoyun R Xu
(74) *Attorney, Agent, or Firm* — MEDLER FERRO WOODHOUSE & MILLS PLLC

(57)          ABSTRACT

Embodiments described herein generally relate to systems and methods for processing mass spectrometry samples. Aspects of the disclosure include systems and methods for processing samples. Additionally, embodiments of the disclosure can also include systems and methods for sample analysis. Various embodiments include data analysis systems and methods for comparing data across samples and sample runs. Data analysis systems can run normalization methods for normalizing raw abundance mass spectrometry data. In some aspects, the normalized data can be used as input for predictive models.

9 Claims, 23 Drawing Sheets

(56) References Cited

U.S. PATENT DOCUMENTS

| | | |
|---|---|---|
| 2020/0372973 A1 | 11/2020 | Serie et al. |
| 2022/0187317 A1 | 6/2022 | Ramachandran et al. |

OTHER PUBLICATIONS

Merleev et al.; A site-specific map of the human plasma glycome and its age and gender-associated alterations; Nature Research, Scientific Reports 10:17505 (2020); also available at URL:https://link.springer.com/content/pdf/10.1038/s41598-020-73588-x.pdf, last visited Sep. 24, 2025.

500

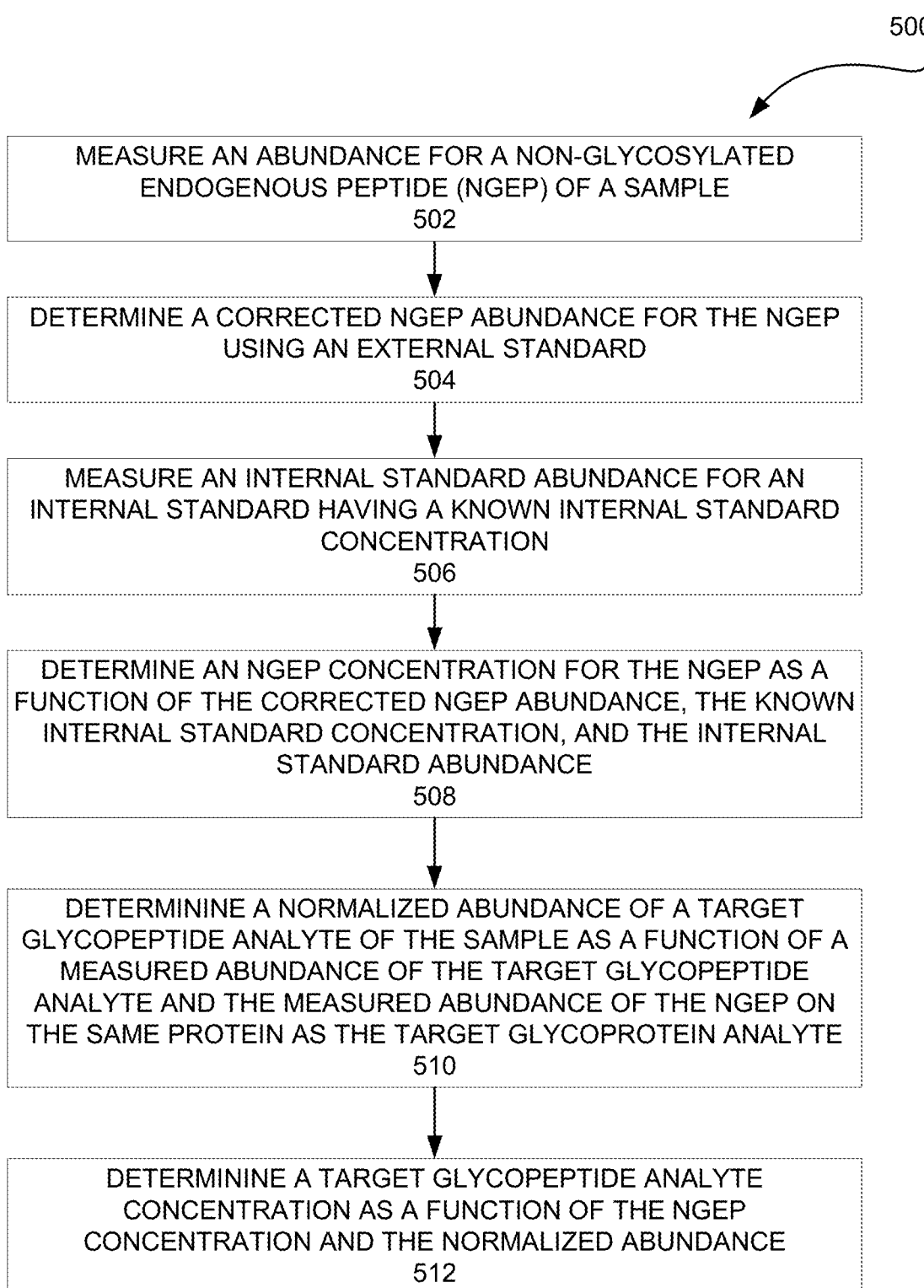

MEASURE AN ABUNDANCE FOR A NON-GLYCOSYLATED
ENDOGENOUS PEPTIDE (NGEP) OF A SAMPLE
502

DETERMINE A CORRECTED NGEP ABUNDANCE FOR THE NGEP
USING AN EXTERNAL STANDARD
504

MEASURE AN INTERNAL STANDARD ABUNDANCE FOR AN
INTERNAL STANDARD HAVING A KNOWN INTERNAL STANDARD
CONCENTRATION
506

DETERMINE AN NGEP CONCENTRATION FOR THE NGEP AS A
FUNCTION OF THE CORRECTED NGEP ABUNDANCE, THE KNOWN
INTERNAL STANDARD CONCENTRATION, AND THE INTERNAL
STANDARD ABUNDANCE
508

DETERMININE A NORMALIZED ABUNDANCE OF A TARGET
GLYCOPEPTIDE ANALYTE OF THE SAMPLE AS A FUNCTION OF A
MEASURED ABUNDANCE OF THE TARGET GLYCOPEPTIDE
ANALYTE AND THE MEASURED ABUNDANCE OF THE NGEP ON
THE SAME PROTEIN AS THE TARGET GLYCOPROTEIN ANALYTE
510

DETERMININE A TARGET GLYCOPEPTIDE ANALYTE
CONCENTRATION AS A FUNCTION OF THE NGEP
CONCENTRATION AND THE NORMALIZED ABUNDANCE
512

Figure 5

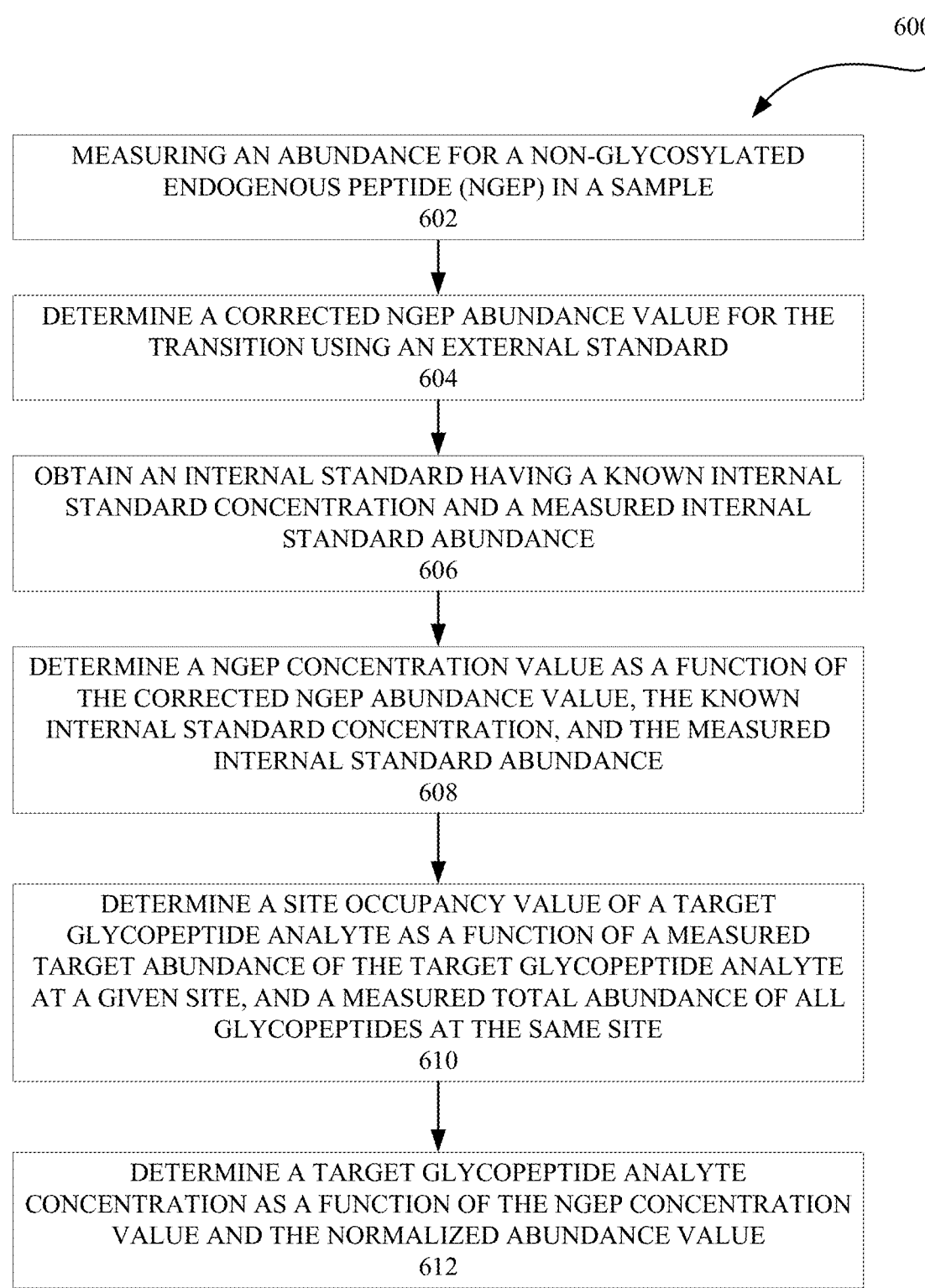

600

MEASURING AN ABUNDANCE FOR A NON-GLYCOSYLATED ENDOGENOUS PEPTIDE (NGEP) IN A SAMPLE
602

DETERMINE A CORRECTED NGEP ABUNDANCE VALUE FOR THE TRANSITION USING AN EXTERNAL STANDARD
604

OBTAIN AN INTERNAL STANDARD HAVING A KNOWN INTERNAL STANDARD CONCENTRATION AND A MEASURED INTERNAL STANDARD ABUNDANCE
606

DETERMINE A NGEP CONCENTRATION VALUE AS A FUNCTION OF THE CORRECTED NGEP ABUNDANCE VALUE, THE KNOWN INTERNAL STANDARD CONCENTRATION, AND THE MEASURED INTERNAL STANDARD ABUNDANCE
608

DETERMINE A SITE OCCUPANCY VALUE OF A TARGET GLYCOPEPTIDE ANALYTE AS A FUNCTION OF A MEASURED TARGET ABUNDANCE OF THE TARGET GLYCOPEPTIDE ANALYTE AT A GIVEN SITE, AND A MEASURED TOTAL ABUNDANCE OF ALL GLYCOPEPTIDES AT THE SAME SITE
610

DETERMINE A TARGET GLYCOPEPTIDE ANALYTE CONCENTRATION AS A FUNCTION OF THE NGEP CONCENTRATION VALUE AND THE NORMALIZED ABUNDANCE VALUE
612

Figure 6

900

RECEIVE RAW ABUNDANCE DATA FOR A SAMPLE FROM A MASS SPECTROMETRY SYSTEM, THE RAW ABUNDANCE DATA COMPRISING: A RAW EXTERNAL STANDARD ABUNDANCE FOR AN EXTERNAL STANDARD IN THE SAMPLE, A RAW INTERNAL STANDARD ABUNDANCE FOR AN INTERNAL STANDARD THAT HAS A KNOWN CONCENTRATION IN THE SAMPLE, A RAW GLYCOPEPTIDE ABUNDANCE FOR A GLYCOPEPTIDE STRUCTURE IN THE SAMPLE, A RAW NON-GLYCOSYLATED PEPTIDE ABUNDANCE FOR A NON-GLYCOSYLATED PEPTIDE STRUCTURE IN THE SAMPLE, THE NON-GLYCOSYLATED PEPTIDE STRUCTURE BEING DERIVED FROM A SAME GLYCOPROTEIN AS THE GLYCOPEPTIDE STRUCTURE
902

COMPUTE CORRECTED ABUNDANCE DATA USING A DIFFERENCE BETWEEN THE RAW EXTERNAL STANDARD ABUNDANCE AND A REFERENCE ABUNDANCE FOR THE EXTERNAL STANDARD
904

GENERATING NORMALIZED CONCENTRATION DATA FOR THE SAMPLE USING THE CORRECTED ABUNDANCE DATA, THE RAW INTERNAL STANDARD ABUNDANCE, THE KNOWN CONCENTRATION OF THE INTERNAL STANDARD, THE RAW GLYCOPEPTIDE ABUNDANCE, AND THE RAW NON-GLYCOSYLATED PEPTIDE ABUNDANCE
906

ANALYZING THE NORMALIZED CONCENTRATION DATA USING A MODEL SYSTEM TO GENERATE AN OUTPUT FOR A SUBJECT
908

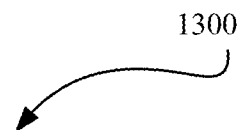

1300

PREPARE RUN SAMPLES FOR TWO OR MORE SAMPLE RUNS FOR LC-MS ANALYSIS, COMPRISING GENERATING A FIRST SET OF RUN SAMPLES, EACH OF THE FIRST SET INCLUDING AN EXTERNAL STANDARD, AND GENERATING A SECOND SET OF RUN SAMPLES, EACH OF THE SECOND SET INCLUDING AT LEAST TWO TARGET GLYCOPEPTIDE ANALYTES AND AN INTERNAL STANDARD
1302

COMBINE AT LEAST TWO RUN SAMPLES OF THE FIRST SET TO CREATE A POOLED STANDARD
1304

ANALYZE EACH RUN SAMPLE ACCORDING TO A RUN ORDER, WHEREIN THE RUN ORDER SPECIFIES A RELATIVE ORDER OF ANALYSIS FOR THE RUN SAMPLES OF THE SAMPLE RUN
1306

NORMALIZE THE RAW ABUNDANCE DATA OF THE TWO OR MORE SAMPLE RUNS BY USING THE POOLED STANDARD OF EACH SAMPLE RUN AS A REFERENCE
1308

Figure 13

| Run order | sample position | New Labels |
|---|---|---|
| 001 | Vial1 | BLANKS_1 |
| 002 | Vial2 | BSA-1 |
| 003 | Vial2 | BSA-1 |
| 004 | Vial2 | BSA-1 |
| 005 | Vial1 | BLANKS_1 |
| 006 | P2-H11 | SS-JAR1-SysEquil |
| 007 | P2-H11 | SS-JAR1-SysEquil |
| 008 | P2-H11 | SS-JAR1-SysEquil |
| 009 | P2-H11 | SS-JAR1-SysEquil |
| 010 | P2-H11 | SS-JAR1-SysEquil |
| 011 | Vial1 | BLANKS_1 |
| 012 | P2-H11 | SS-JAR1-SysSuit |
| 013 | P1-A1 | SS-JAR1-SS01 |
| 014 | P1-A12 | SS-JAR1-SS02 |
| 015 | P1-B11 | SS-JAR1-SS03 |
| 016 | P1-C10 | SS-JAR1-SS04 |
| 017 | P1-D9 | SS-JAR1-SS05 |
| 018 | P1-E8 | SS-JAR1-SS06 |
| 019 | P1-F7 | SS-JAR1-SS07 |
| 020 | P1-G6 | SS-JAR1-SS08 |
| 021 | P1-H5 | SS-JAR1-SS09 |
| 022 | Vial1 | BLANKS_1 |
| 023 | P2-H11 | SS-JAR1-SysSuit |
| 024 | P2-A4 | SS-JAR1-SS10 |
| 025 | P2-B3 | SS-JAR1-SS11 |
| 026 | P2-C2 | SS-JAR1-SS12 |
| 027 | P2-D1 | SS-JAR1-SS13 |
| 028 | P2-D12 | SS-JAR1-SS14 |
| 029 | P2-E11 | SS-JAR1-SS15 |
| 030 | P2-F10 | SS-JAR1-SS16 |
| 031 | P2-G9 | SS-JAR1-SS17 |
| 032 | P2-H8 | SS-JAR1-SS18 |

| Run order | sample position | New Labels |
|---|---|---|
| 033 | Vial1 | BLANKS_1 |
| 034 | P2-H11 | SS-JAR1-SysSuit |
| 035 | P1-A1 | SS-JAR1-SS01 |
| 036 | P2-C6 | HVI-CRC-51 |
| 037 | P2-H2 | IND-CR1-51 |
| 038 | P1-F12 | iSP-OV1-100 |
| 039 | P2-B9 | HVI-CRC-350 |
| 040 | P2-E1 | STA-AGE-20 |
| 041 | P1-H7 | STA-AGE-23 |
| 042 | P1-G4 | HVI-CRC-352 |
| 043 | P2-H4 | HVI-CRC-348 |
| 044 | P1-D1 | HVI-CRC-229 |
| 045 | P1-H10 | STA-AGE-37 |
| 046 | Vial1 | BLANKS_1 |
| 047 | P2-H11 | SS-JAR1-SysSuit |
| 048 | P1-A12 | SS-JAR1-SS02 |
| 049 | P1-B1 | HVI-CRC-169 |
| 050 | P1-B12 | HVI-CRC-353 |
| 051 | P1-A6 | STA-AGE-44 |
| 052 | P2-D4 | HVI-CRC-264 |
| 053 | P2-H3 | IND-CR1-23 |
| 054 | P1-B6 | STA-AGE-46 |
| 055 | P2-G11 | STA-AGE-7 |
| 056 | P1-F11 | PAL-HYD-38 |
| 057 | P1-G10 | HVI-CRC-383 |
| 058 | P1-G2 | IND-CR1-10 |
| 059 | Vial1 | BLANKS_1 |
| 060 | P2-H11 | SS-JAR1-SysSuit |
| 061 | P1-B11 | SS-JAR1-SS03 |
| 062 | P2-F3 | STA-AGE-14 |
| 063 | P2-A2 | HVI-CRC-263 |
| 064 | P2-C4 | STA-AGE-49 |

| Run order | sample position | New Labels |
|---|---|---|
| 236 | P1-E7 | HVI-CRC-300 |
| 237 | P1-C1 | HVI-CRC-360 |
| 238 | P2-D8 | HVI-CRC-293 |
| 239 | P1-A11 | STA-AGE-13 |
| 240 | P1-H8 | HVI-CRC-81 |
| 241 | Vial1 | BLANKS_1 |
| 242 | P2-H11 | SS-JAR1-SysSuit |
| 243 | P2-G9 | SS-JAR1-SS17 |
| 244 | P1-F9 | HVI-CRC-89 |
| 245 | P2-E3 | HVI-CRC-237 |
| 246 | P2-B4 | IND-CR1-13 |
| 247 | P2-G8 | HVI-CRC-49 |
| 248 | P2-E10 | IND-CR1-27 |
| 249 | P1-B7 | STA-AGE-16 |
| 250 | P2-G3 | IND-CR1-6 |
| 251 | P1-D8 | HVI-CRC-79 |
| 252 | P1-E4 | STA-AGE-11 |
| 253 | P1-C12 | HVI-CRC-69 |
| 254 | Vial1 | BLANKS_1 |
| 255 | P2-H11 | SS-JAR1-SysSuit |
| 256 | P2-H8 | SS-JAR1-SS18 |
| 257 | Vial1 | BLANKS_1 |
| 258 | P2-H11 | SS-JAR1-SysSuit |
| 259 | Vial1 | BLANKS_1 |
| 260 | Vial1 | BLANKS_1 |
| 261 | Vial2 | BSA-1 |
| 262 | Vial2 | BSA-1 |
| 263 | Vial2 | BSA-1 |
| 264 | Vial1 | BLANKS_1 |
| 265 | Vial1 | BLANKS_1 |
| 266 | Vial1 | BLANKS_1 |
| 267 | Vial1 | BLANKS_1 |

Figure 16

Plate 1

|   | 1 | 2 | 3 | 4 | 5 | 6 | 7 | 8 | 9 | 10 | 11 | 12 |
|---|---|---|---|---|---|---|---|---|---|----|----|----|
| A | SS01 | AF005 | AK215 | AK381 | AK101 | Z044 | AK373 | AK057 | S092 | AK273 | Z013 | SS02 |
| B | AK169 | AF062 | Z017 | AK119 | Q049 | Z046 | Z016 | Z045 | Z024 | AK218 | SS03 | AK353 |
| C | AK360 | Z043 | Z002 | AK359 | Z031 | Q043 | AK386 | AK052 | AK030 | SS04 | AF012 | AK069 |
| D | AK229 | Z042 | AK333 | Z048 | AK299 | AK281 | Z034 | AK079 | SS05 | AK055 | AF004 | AK200 |
| E | Q046 | Z015 | AK274 | Z011 | AK212 | AK033 | AK300 | SS06 | AF028 | AK086 | AK006 | AK103 |
| F | AK029 | AK010 | AK337 | AK217 | AK335 | AF052 | SS07 | AK130 | AK089 | AK266 | Q038 | S100 |
| G | S129 | AF010 | Z035 | AK352 | AK068 | SS08 | AK356 | AK222 | AK170 | AK383 | AF022 | AK221 |
| H | Z001 | AK246 | Z029 | AK326 | SS09 | AK042 | Z023 | AK081 | AK191 | Z037 | S128 | AF045 |

Plate 2

|   | 1 | 2 | 3 | 4 | 5 | 6 | 7 | 8 | 9 | 10 | 11 | 12 |
|---|---|---|---|---|---|---|---|---|---|----|----|----|
| A | AK053 | AK263 | AF019 | SS10 | AK168 | AK285 | AK092 | AK369 | Z047 | AK272 | AK111 | AK098 |
| B | AF043 | Q050 | SS11 | AF013 | AK134 | AK322 | Z003 | AK196 | AK350 | AK249 | AK073 | AK344 |
| C | Z032 | SS12 | AK060 | Z049 | AK232 | AK051 | AK071 | Z008 | AK192 | S109 | AK129 | AK288 |
| D | SS13 | AF042 | AK062 | AK264 | AK026 | AK133 | AK284 | AK293 | AK380 | Z038 | AK189 | SS14 |
| E | Z020 | S095 | AK237 | AK270 | AK298 | AK339 | AF053 | AK082 | Q053 | AF027 | SS15 | AK138 |
| F | AK324 | S099 | Z014 | Z018 | S122 | AK016 | AK278 | AK376 | S102 | SS16 | AK207 | AK312 |
| G | AK362 | AK185 | AF006 | AF068 | AK201 | AK070 | Z022 | AK049 | SS17 | Z027 | Z007 | Q054 |
| H | Q044 | AF051 | AF023 | AK348 | AK219 | Z021 | AF021 | SS18 | AF026 | AF063 | SS | SS |

SYSTEMS AND METHODS FOR GLYCOPEPTIDE CONCENTRATION DETERMINATION, NORMALIZED ABUNDANCE DETERMINATION, AND LC/MS RUN SAMPLE PREPARATION

CROSS-REFERENCE TO RELATED APPLICATIONS

This application claims priority to U.S. Provisional Patent Application Ser. No. 63/251,028, filed Sep. 30, 2021, and also claims priority to U.S. Provisional Patent Application Ser. No. 63/293,506, filed Dec. 23, 2021, both of which applications are incorporated herein in their entirety.

FIELD

This description is generally directed towards systems and methods for normalizing raw abundance data generated using mass spectrometry.

BACKGROUND

Protein glycosylation and other post-translational modifications play vital roles in virtually all aspects of human physiology. Unsurprisingly, faulty or altered protein glycosylation often accompanies various phenotypes (e.g. disease states). The identification of aberrant glycosylation provides opportunities for early detection, intervention, and treatment of affected subjects.

Protein glycosylation data can be used to train predictive models for identifying phenotypes of subjects based on the subject's protein glycosylation profile. Predictive models make better predictions using large quantities of high-quality data, however, making comparisons across multiple experiments or between samples can be challenging in a variety of fields, including the field of mass spectrometry. A variety of factors can make comparisons difficult, including, but not limited to variation in several of the sample preparation and sample collection steps between experiments and samples. More specifically, efficiency of trypsin digest, ionization efficiency, detector efficiency, and other contributing factors can lead to a high degree of variability, thereby, making existing systems and methods for normalizing data between samples and experiments either cost prohibitive or non-existent.

In light of the above, there is a need for improved data relativization and normalization systems and methods so that high-quality, comparative data can be used in building predictive models. The present disclosure addresses this and other needs by providing systems and methods for comparing glycosylation data across samples and across multiple experiments. More specifically, the present disclosure includes systems and methods for relativizing and normalizing protein glycosylation data to better train predictive models.

There is also a further need for new sample preparation and processing methods and systems addressing the current challenges involving data normalization in existing systems. Specifically, the industry needs effective standards for normalizing abundance with samples and between samples. The systems and methods described herein address those needs and more.

SUMMARY

In various aspects, a method of determining a concentration of a target glycopeptide analyte in a sample is described. In various embodiments, the method can comprise measuring an abundance for a non-glycosylated endogenous peptide (NGEP) of a sample. In some embodiments, the method can comprise, determining a corrected NGEP abundance for the NGEP using an external standard. In some embodiments, the method can comprise, measuring an internal standard abundance for an internal standard having a known internal standard concentration. In some embodiments, the method can comprise, determining an NGEP concentration for the NGEP as a function of the corrected NGEP abundance, the known internal standard concentration, and the internal standard abundance. In some embodiments, the method can comprise, determining a normalized abundance of a target glycopeptide analyte of the sample as a function of a measured abundance of the target glycopeptide analyte and the measured abundance of the NGEP on the same protein as the target glycoprotein analyte. In some embodiments, the method can comprise determining a target glycopeptide analyte concentration as a function of the NGEP concentration and the normalized abundance.

In some aspects, a non-transitory computer-readable medium storing computer instructions that, when executed by a computer, cause the computer to perform a method for determining a concentration of a target glycopeptide analyte of the sample in a sample is described. In various embodiments, the method can comprise, measuring an abundance for a non-glycosylated endogenous peptide (NGEP) in a sample. In various embodiments, the method can comprise, determining a corrected NGEP abundance for the NGEP using an external standard. In various embodiments, the method can comprise, measuring an internal standard abundance for an internal standard having a known internal standard concentration. In various embodiments, the method can comprise, determining an NGEP concentration as a function of the corrected NGEP abundance, the known internal standard concentration, and the internal standard abundance. In various embodiments, the method can comprise, determining a normalized abundance of a target glycopeptide analyte of the sample as a function of a measured abundance of the target glycopeptide analyte and the measured abundance of the non-glycosylated endogenous peptide (NGEP) on the same protein as the target glycoprotein analyte. In various embodiments, the method can comprise, determining a target glycopeptide analyte concentration as a function of the NGEP concentration and the normalized abundance.

In various aspects, a method of determining a concentration of a target glycopeptide analyte in a sample is described. In various embodiments, the method can comprise measuring an abundance for a NGEP of a sample. In various embodiments, the method can comprise determining a corrected NGEP abundance for the NGEP using an external standard. In various embodiments, the method can comprise measuring an internal standard abundance for an internal standard having a known internal standard concentration. In various embodiments, the method can comprise determining a NGEP concentration as a function of the corrected NGEP abundance, the known internal standard concentration, and the internal standard abundance. In various embodiments, the method can comprise determining a site occupancy of a target glycopeptide analyte of the sample as a function of a measured target abundance of the target glycopeptide analyte at a given site, and a measured total abundance of all glycopeptides quantified at the same site. In various embodiments, the method can comprise determining a target glycopeptide analyte concentration as a function of the NGEP concentration and the normalized abundance.

In various aspects, a non-transitory computer-readable medium storing computer instructions that, when executed by a computer, cause the computer to perform a method for determining a concentration of a target glycopeptide analyte of a sample is described. In various embodiments, the method can comprise, measuring an abundance for a non-glycosylated endogenous peptide (NGEP) of a sample. In various embodiments, the method can comprise, determining a corrected NGEP abundance for the NGEP using an external standard. In various embodiments, the method can comprise, measuring an internal standard abundance for an internal standard having a known internal standard concentration. In various embodiments, the method can comprise, determining a NGEP concentration as a function of the corrected NGEP abundance, the known internal standard concentration, and the internal standard abundance. In various embodiments, the method can comprise, determining a site occupancy of a target glycopeptide analyte of the sample as a function of a measured target abundance of the target glycopeptide analyte at a given site, and a measured total abundance of all glycopeptides at the same site. In various embodiments, the method can comprise, determining a target glycopeptide analyte concentration as a function of the NGEP concentration and the normalized abundance.

In some aspects, a method for preparing samples for a liquid chromatography/mass spectrometry (LC-MS) sample run and normalizing abundance data of a plurality of sample runs is described in accordance with various embodiments. In some embodiments, the method comprises preparing run samples for the plurality of sample runs for LC-MS analysis. In various embodiments, the step of preparing comprises generating a first set of run samples. In various embodiments, each of the first set of run samples includes an external standard. In various embodiments the step of preparing comprises generating a second set of run samples. In various embodiments, each of the second set of run samples includes at least two target glycopeptide analytes and an internal standard. In various embodiments, the method comprises combining at least two run samples of the first set of run samples to create a pooled standard. In various embodiments, the method comprises analyzing each run sample according to a run order. In various embodiments, the run order specifies a relative order of analysis for the run samples of the sample run. In various embodiments, the method comprises normalizing the raw abundance data of the plurality of sample runs using the pooled standard of each sample run as a reference.

In some aspects, a sample processing system for carrying out a process for preparing samples for a liquid chromatography/mass spectrometry (LC-MS) sample run and normalizing abundance data of a plurality of sample runs is described in accordance with various embodiments. In various embodiments, the sample processing system comprises a sample preparation system. In various embodiments, the sample preparation system includes a fluidic instrument for performing a process. In various embodiments, the process can comprise generating a first set of run samples. In various embodiments, each of the first set includes an external standard. In various embodiments, the process can comprise generating a second set of run samples. In various embodiments, each of the second set includes at least two target glycopeptide analytes and an internal standard. In various embodiments, the process can comprise combining at least two run samples of the first set to create a pooled standard. In various embodiments, the sample processing system can comprise a sample analysis system. In various embodiments, the sample analysis system can include a LC-MS instrument for analyzing glycopeptide analytes. In various embodiments, the sample analysis system can analyze each run sample according to a run order. In various embodiments, the run order can be stored on a data store in electronic communication with the LC-MS instrument and specifies a relative order of analysis for the run samples of the sample run. In various embodiments, the sample processing system comprises a data analysis system, including a normalization module of a peptide structure analyzer, for normalizing raw abundance data of the plurality of sample runs using the pooled standard of each sample run as a common reference.

BRIEF DESCRIPTION OF THE DRAWINGS

The present disclosure is described in conjunction with the appended figures:

FIG. 5 is flowchart of a process for determining a concentration of a target glycopeptide analyte in a sample in accordance with various embodiments.

FIG. 6 is a flowchart of a process for determining a concentration of a target glycopeptide analyte in a sample in accordance with various embodiments.

FIG. 9 is a flowchart of a process for determining a concentration of a target glycopeptide analyte in a sample is described in accordance with various embodiments.

FIG. 12A and FIG. 12B illustrate confusion matrices resulting in applying a trained ovarian cancer model to an independent test set and demonstrate an increase in predictive accuracy using the systems and methods described herein and in accordance with various embodiments.

FIG. 13 illustrates a flowchart of an exemplary method for preparing samples for a LC-MS sample run and normalizing abundance data of a plurality of sample runs.

FIG. 16 illustrates an experimental run order for a set of run samples.

FIG. 17 illustrates a layout for a 96-well plate including run sample partition locations.

DETAILED DESCRIPTION

I. Overview

Figure 1:
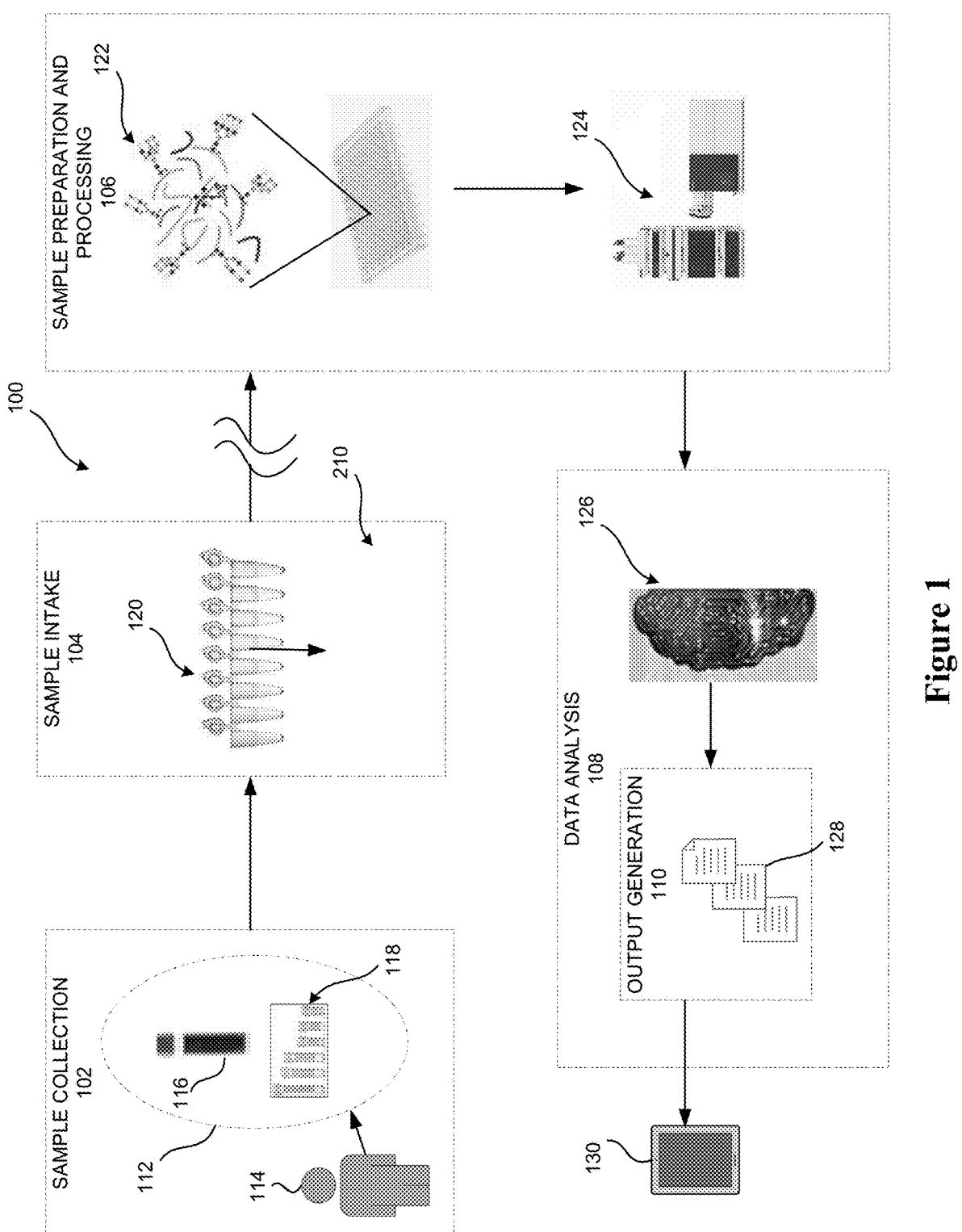
FIG. 1 is a schematic diagram of an exemplary workflow 100 for the detection of peptide structures associated with a disease state for use in diagnosis and/or treatment in accordance with one or more embodiments.

The embodiments described herein recognize that glycoproteomics is an emerging field that can be used in the overall diagnosis and/or treatment of subjects with various types of diseases. Glycoproteomics aims to determine the positions, identities, and quantities of glycans and glycosylated proteins in a given sample (e.g., blood sample, cell, tissue, etc.). Protein glycosylation is one of the most common and most complex forms of post-translational protein modification, and can affect protein structure, conformation, and function. For example, glycoproteins may play crucial roles in important biological processes such as cell signaling, host-pathogen interactions, and immune response and disease. Glycoproteins may therefore be important to diagnosing different types of diseases or disease states.

In using this emerging technology to its full potential, supplying large quantities of high-quality abundance data to a predictive model can improve the predictive accuracy of the model. However, raw glycopeptide abundance data may be difficult to compare across different experiments or even samples within the same experiment. The skilled artisan can appreciate that improved relativizing and normalizing data systems and methods can be a way to manage such variation. Additionally, sample preparation and processing systems and methods are necessary to generate optimal data for undergoing data analysis.

Accordingly, the embodiments described herein provide various methods and systems sample preparation and processing, including, various normalization systems and methods.

The description below provides exemplary implementations of the methods and systems described herein for the data processing. Descriptions and examples of various terms, as used herein, are provided in Section II below.

II. Exemplary Descriptions of Terms

As used herein, "abundance," may refer to a quantitative value generated using mass spectrometry. In various embodiments, the quantitative value may relate to the amount of a particular peptide structure. In some embodiments, the quantitative value may comprise an amount of an ion produced using mass spectrometry. In some embodiments, the quantitative value may be expressed as an m/z value. In other embodiments, the quantitative value may be expressed in atomic mass units.

The term "alkylation," as used herein, generally refers to the transfer of an alkyl group from one molecule to another. In various embodiments, alkylation is used to react with reduced cysteines to prevent the re-formation of disulfide bonds after reduction has been performed.

The term "amino acid," as used herein, generally refers to any organic compound that includes an amino group (e.g. —NH2), a carboxyl group (—COOH), and a side chain group (R) which varies based on a specific amino acid. Amino acids can be linked using peptide bonds.

As used herein, an "artificial neural network" or "neural network" (NN) may refer to mathematical algorithms or computational models that mimic an interconnected group of artificial nodes or neurons that processes information based on a connectionistic approach to computation. Neural networks, which may also be referred to as neural nets, can employ one or more layers of nonlinear units to predict an output for a received input. Some neural networks include one or more hidden layers in addition to an output layer. The output of each hidden layer is used as input to the next layer in the network, i.e., the next hidden layer or the output layer. Each layer of the network generates an output from a received input in accordance with current values of a respective set of parameters. In the various embodiments, a reference to a "neural network" may be a reference to one or more neural networks.

A neural network may process information in two ways: when it is being trained it is in training mode and when it puts what it has learned into practice, it is in inference (or prediction) mode. Neural networks learn through a feedback process (e.g., backpropagation) which allows the network to adjust the weight factors (modifying its behavior) of the individual nodes in the intermediate hidden layers so that the output matches the outputs of the training data. In other words, a neural network learns by being fed training data (learning examples) and eventually learns how to reach the correct output, even when it is presented with a new range or set of inputs. A neural network may include, for example, without limitation, at least one of a Feedforward Neural Network (FNN), a Recurrent Neural Network (RNN), a Modular Neural Network (MNN), a Convolutional Neural Network (CNN), a Residual Neural Network (ResNet), an Ordinary Differential Equations Neural Networks (neural-ODE), or another type of neural network.

As used herein, the phrase "at least one of," when used with a list of items, means different combinations of one or more of the listed items may be used and only one of the items in the list may be needed. The item may be a particular object, thing, step, operation, process, or category. In other words, "at least one of" means any combination of items or number of items may be used from the list, but not all of the items in the list may be required. For example, without limitation, "at least one of item A, item B, or item C" means item A; item A and item B; item B; item A, item B, and item C; item B and item C; or item A and C. In some cases, "at least one of item A, item B, or item C" means, but is not limited to, two of item A, one of item B, and ten of item C; four of item B and seven of item C; or some other suitable combination.

The term "biomarker," as used herein, generally refers to any measurable substance taken as a sample from a subject whose presence is indicative of some phenomenon. Non-limiting examples of such phenomenon can include a healthy state, a disease state, a condition, or exposure to a compound or environmental condition. In various embodiments described herein, biomarkers may be used for diagnostic purposes. Biomarkers can be used to diagnose a state of a subject such as, for non-limiting examples, a healthy state or a disease state.

The term "denaturation," as used herein, generally refers to any molecule that loses quaternary structure, tertiary structure, and secondary structure which is present in their native state. Non-limiting examples include proteins or nucleic acids being exposed to an external compound or environmental condition such as acid, base, temperature, pressure, radiation, etc.

The term "denatured protein," as used herein, generally refers to a protein that loses quaternary structure, tertiary structure, and secondary structure which is present in their native state.

The terms "digestion" or "enzymatic digestion," as used herein, generally refer to breaking apart a polymer (e.g. cutting a polypeptide at a cut site). Proteins may be digested in preparation for mass spectrometry using trypsin digestion protocols. Proteins may be digested using other proteases in preparation for mass spectrometry if access is limited to cleavage sites.

The term "disease state" as used herein, generally refers to a condition that affects the structure or function of an organism. Non-limiting examples of causes of disease states may include pathogens, immune system dysfunctions, cell damage caused by aging, cell damage caused by other factors (e.g. trauma and cancer). Disease states can include any state of a disease whether symptomatic or asymptomatic. Disease states can include disease stages of a disease progression. Disease states can cause minor, moderate, or severe disruptions in structure or function of an organism (e.g. a subject).

As used herein, "external standard," may refer to a standard used to normalize data from one sample run to another sample run. In various embodiments, an external standard can include a NGEP. A run sample can include and external standard. An external standard can include the same or a similar structure to the target glycopeptide analyte. An external standard source may include multiple external standards. External standards can be run independently of patient samples. External standard sources can be added to a run sample for sample processing and data collection. For example, a processing step may include enzymatic digestion of one or more glycoproteins using enzymatic digestion to produce one or more external standards or external standard analytes. A sample run can include a plurality of run samples including an external standard. Abundance data collected from external standards can be used to normalize raw abundance originating from target glycopeptide analytes of the run samples. Portions of a plurality of run samples including the external standard can be pooled to generate a pooled standard. Serum can be a source for external standards and can be available through commercial suppliers (e.g., Sigma-Aldrich™). Pooled standard can be used to compare run samples between sample runs.

The terms "glycan," as used herein, generally refers to a glycoconjugate such as a carbohydrate that is covalently linked to another biological molecule. Carbohydrates can include monosaccharides, disaccharides, oligosaccharides, or polysaccharides. The biological molecule can include a residue of an amino acid of a protein or polypeptide. Glycans can be covalently attached to a side chain (i.e. R group) of an amino acid residue of a glycopeptide.

The terms "glycopeptide" or "glycopolypeptide" as used herein, generally refers to a peptide or polypeptide comprising at least one glycan located at one or more residues of the peptide or polypeptide.

The term "glycoprotein," as used herein, generally refers to a protein having at least one glycan residue bonded thereto. In some examples, a glycoprotein is a protein with at least one oligosaccharide chain covalently bonded thereto. Examples of glycoproteins, include but are not limited to apolipoprotein C-III (APOC3), alpha-1-antichymotrypsin (AACT), afamin (AFAM), alpha-1-acid glycoprotein 1 & 2 (AGP12), apolipoprotein B-100 (APOB), apolipoprotein D (APOD), complement C1s subcomponent (C1S), calpain-3 (CAN3), clusterin (CLUS), complement component C8AChain (CO8A), alpha-2-HS-glycoprotein (FETUA), haptoglobin (HPT), immunoglobulin heavy constant gamma 1 (IgG1), immunoglobulin J chain (IgJ), plasma kallikrein (KLKB1), serum paraoxonase/arylesterase 1 (PON1), prothrombin (THRB), serotransferrin (TRFE), protein unc-13 homologA (UN13A), and zinc-alpha-2-glycoprotein (ZA2G). A glycopeptide, as used herein, refers to a fragment of a glycoprotein, unless specified otherwise to the contrary.

As used herein, an "internal standard," may refer to a molecule that can be contained (e.g. added-to or spiked-into) in the same sample as a target glycopeptide analyte undergoing mass spectrometry analysis. Internal standards can be spiked into all patient samples. Internal standards can also be spiked into run samples including external standards. Many internal standards can include peptides or glycopeptides. Some peptides can include glycosylation sites. For various applications, peptides used as an internal standard can be non-glycosylated at one or more glycosylation sites. Internal standards can be used for calibration purposes. Internal standards can be used for normalization and quantification. The systems and methods herein can use non-glycosylated peptides and/or non-glycosylated endogenous peptides. When collecting data that may need to be normalized and quantified, each target glycosylation site can have an internal standard for comparison. In many cases, a glycoproteins being analyzed may include a corresponding aglycosylated version for comparison. In place of an internal standard having the same structure as a target glycopeptide analyte, an surrogate internal standard can be used for the target glycopeptide analyte, wherein the internal standard includes a similar m/z ratio and or retention time to the target glycopeptide analyte. In various embodiments, internal standards are spiked into all run samples comprising glycopeptide analytes undergoing mass spectrometry interrogation.

The term "linking site" or "glycosylation site" as used herein generally refers to the location where a sugar molecule of a glycan or glycan structure is directly bound (e.g. covalently bound) to an amino acid of a peptide, a polypeptide, or a protein. For example, the linking site may be an amino acid residue and a glycan structure may be linked via an atom of the amino acid residue. Non-limiting examples of types of glycosylation can include N-linked glycosylation, O-linked glycosylation, C-linked glycosylation, S-linked glycosylation, and glycation.

The term "liquid chromatography," as used herein, generally refers to a technique used to separate a sample into parts. Liquid chromatography can be used to separate, identify, and quantify components.

As used herein, "machine learning" may be the practice of using algorithms to parse data, learn from it, and then make a determination or prediction about something in the world. Machine learning uses algorithms that can learn from data without relying on rules-based programming. A machine learning algorithm may include a parametric model, a non-parametric model, a deep learning model, a neural network, a linear discriminant analysis model, a quadratic discriminant analysis model, a support vector machine, a random forest algorithm, a nearest neighbor algorithm, a combined discriminant analysis model, a k-means clustering algorithm, a supervised model, an unsupervised model, logistic regression model, a multivariable regression model, a penalized multivariable regression model, or another type of model.

The term "mass spectrometry," as used herein, generally refers to an analytical technique used to identify molecules. In various embodiments described herein, mass spectrometry can be involved in characterization and sequencing of proteins.

As used herein, a "model" may include one or more algorithms, one or more mathematical techniques, one or more machine learning algorithms, or a combination thereof.

The term "m/z" or "mass-to-charge ratio" as used herein, generally refers to an output value from a mass spectrometry instrument. In various embodiments, m/z can represent a relationship between the mass of a given ion and the number of elementary charges that it carries. The "m" in m/z stands for mass and the "z" standards for charge number of ions. In some embodiments, m/z can be displayed on an x-axis of a mass spectrum.

As used herein, a "non-glycosylated endogenous peptide" ("NGEP"), may refer to a peptide structure including glycosylation sites at a location of one or more amino acids. In various embodiments, one or more glycosylation sites can be non-glycosylated (e.g., do not include a glycan molecule) for a given NGEP. A NGEP and a target glycopeptide analyte can originate from the same subject. A NGEP and a target glycopeptide analyte can originate from the same protein. A NGEP and a target glycopeptide analyte can originate from the different proteins. Peptide structures, including NGEPs, can be labeled with an isotope in preparation for mass spectrometry analysis. NGEPs can be used as internal standards for the systems and methods described herein.

The term "ones" means more than one.

The terms "peptides" or "polypeptide" as used herein, can be used interchangeably, and generally refer to amino acids linked by peptide bonds. Peptides can include amino acid chains between 10 and 50 residues. Peptides can include amino acid chains shorter than 10 residues, including, oligopeptides, dipeptides, tripeptides, and tetrapeptides. Peptides can include chains longer than 50 residues and may be referred to as "proteins." Proteins may be digested in preparation for mass spectrometry using trypsin digestion protocols. Protocols include digesting protein using proteases in preparation for mass spectrometry. Proteases can be used if access to cleavage sites is limited.

The term "peptide structure," as used herein, generally refers to peptides or a portion thereof or glycopeptides or a portion thereof. In various embodiments described herein, a peptide structure can include any molecule comprising at least two amino acids in sequence.

As used herein, the term "plurality" may be 2, 3, 4, 5, 6, 7, 8, 9, 10, or more.

As used herein, a "peptide structure data," may refer to any data of or relating to a peptide from a resulting mass spectrometry run. A peptide data set can comprise data obtained from a run sample including a sample and/or one or more standards. Peptide structure data can include raw abundance and/or abundance data for external standards, internal standards, and/or target glycopeptide analytes. In some cases, target glycopeptide analytes can originate from a patient sample.

As used herein, a "pooled standard," may refer to a standard created by combining portions of plurality of external standard digests from plurality of run samples. Abundance data from pooled standards originating from different samples runs can be used to normalize abundance data between sample runs, thereby, allowing comparison of glycopeptide analyte abundance data collected at different time points and/or from different experiments.

In many sample runs, one or more individual digestion replicates can be added to plurality of run samples and the abundance data generated can be used to normalize glycopeptide analyte data across a sample run. Run sample data originating from individual digestion replicates can be used to one or more runs including the pooled serum digest (e.g., plurality of individual digestion replicates combined). Many sample runs can include one or more pooled serum digests analyzed at the end of a run order. The abundances from the pooled digests can be compared to the abundances of the one or more individual digestion replicates to normalize raw abundance data for a sample run.

The term "reduction," as used herein, generally refers to the gain of an electron by a substance. In various embodiments described herein, a sugar can directly bind to a protein, thereby, reducing the amino acid to which it binds. Such reducing reactions can occur in glycosylation. In various embodiments, reduction may be used to break disulfide bonds between two cysteines.

As used herein, "relative abundance," may refer to a relationship between plurality of abundances. In some cases, relative abundance can include a comparison of a proportion of one peptide structure to another peptide structure. In some cases, relative abundance can include comparing a proportion of a peptide structure to a total number of peptide structures without having actual values. In some embodiments, the comparison may comprise comparing one peptide glycoform (e.g. two identical peptides differing by one or more glycans) to a set of peptide glycoforms. In some embodiments, the comparison may comprise comparing a number of ions having a particular m/z ratio by a total number of ions detected. In various embodiments, a relative abundance can be expressed as a ratio. In other embodiments, a relative abundance can be expressed as a percentage. Relative abundance can be presented on a y-axis of a mass spectrum plot.

The term "sequence," as used herein, generally refers to a biological sequence including one-dimensional monomers that can be assembled to generate a polymer. Non-limiting examples of sequences include nucleotide sequences (e.g. ssDNA, dsDNA, and RNA), amino acid sequences (e.g. proteins, peptides, and polypeptides), and carbohydrates (e.g. compounds including $C_m (H_2O)_n$).

The terms "sample," "biological sample," "biological specimen," or "biospecimen" as used herein, generally refers to a specimen taken by sampling so as to be representative of the source of the specimen, typically, from a subject. The sample can be representative of an organism as a whole, specific tissue, cell type, or category or subcategory of interest. The sample may include blood. The blood of the sample can include whole blood. The blood of the sample can include plasma. The sample can include a macromolecule. The sample can include a small molecule. The sample can include a virus. The sample can include a cell or derivative of a cell. The sample can include an organelle. The sample can include a cell nucleus. The sample can include a rare cell from a population of cells. The sample can include any type of cell, including without limitation prokaryotic cells, eukaryotic cells, bacterial, fungal, plant, mammalian, or other animal cell type, mycoplasmas, normal tissue cells, tumor cells, or any other cell type, whether derived from single cell or multicellular organisms. The sample can include a constituent of a cell. The sample can include nucleotides (e.g. ssDNA, dsDNA, RNA), organelles, amino acids, peptides, proteins, carbohydrates, glycoproteins, or any combination thereof. The sample can include a matrix (e.g., a gel or polymer matrix) comprising a cell or one or more constituents from a cell (e.g., cell bead), such as DNA, RNA, organelles, proteins, or any combination thereof, from the cell. The sample may be obtained from a tissue of a subject. The sample can include a cell. Such cells may or may not include a cell wall or cell membrane. The sample can include one or more constituents of a cell but may not include other constituents of the cell. An example of such constituents may include a nucleus or an organelle. The biological sample may include a live cell. The live cell can be capable of being cultured.

The sample may be derived from another sample. The sample may include a tissue sample, such as a biopsy, core biopsy, needle aspirate, or fine needle aspirate. The sample may include a fluid sample, such as a blood sample, urine sample, or saliva sample. The sample may include a skin sample. The sample may include a cheek swab. The sample may include a cell-free or cell free sample. A cell-free sample may include extracellular polynucleotides. The sample may originate from blood, plasma, serum, urine, saliva, mucosal excretions, sputum, stool, or tears. The sample may originate from red blood cells or white blood cells. The sample may originate from feces, spinal fluid, CNS fluid, gastric fluid, amniotic fluid, cyst fluid, peritoneal fluid, marrow, bile, other body fluids, tissue obtained from a biopsy, skin, or hair.

As used herein, "sample run," refers to a grouping or set of one or more run samples scheduled to undergo mass spectrometry analysis. For example, at the beginning of a sample run, run samples including material for calibration or instrument maintenance (e.g.,bovine serum albumin (BSA), standards, or blanks) can be processed or/and analyzed by a mass spectrometry instrument for the analysis. Run samples can include patient samples combined with internal standards. Run samples can include external standards. Run samples can be stored in vials or partitions of plates (e.g., a partition of a 96-well plate). In some cases, an automated system including a pipette robot can be programmed to process run samples of a sample run according to a run order.

As used herein, the term "set of" means one or more. For example, a set of items includes one or more items.

The term "subject," as used herein, generally refers to an animal, such as a mammal (e.g., human) or avian (e.g., bird), or other organism, such as a plant. For example, the subject can include a vertebrate, a mammal, a rodent (e.g., a mouse), a primate, a simian or a human. Animals may include, but are not limited to, farm animals, sport animals, and pets. A subject can include a healthy or asymptomatic individual, an individual that has or is suspected of having a disease (e.g., cancer) or a pre-disposition to the disease, and/or an individual that is in need of therapy or suspected of needing therapy. A subject can be a patient. A subject can include a microorganism or microbe (e.g., bacteria, fungi, archaea, viruses). A sample, or constituent thereof, from a subject may be undergo mass spectrometry analysis, thereby, generating peptide structure data for one or more glycopeptides of the sample.

As used herein, a "target glycopeptide analyte," may refer to a peptide structure (e.g., glycosylated or aglycosylated/non-glycosylated) or a fraction of a peptide structure. Target analytes can include sub-structure associated with one or more residues of peptide sequence of the peptide structure (e.g. a glycan associated with a glycosylation site). Target glycopeptide analytes can include a product of one or more of the above listed structures and/or sub-structures. Target glycopeptide analytes can include or be associated with one or more detection molecule (e.g. signal molecule, label, or tag). Target glycopeptide analytes can be prepared using the sample preparation methods and systems described herein. Target glycopeptide analytes can be analyzed with a mass spectrometry system generating raw abundance data for the glycopeptide analyte which can later be normalized using the methods and systems described herein.

The term "training data," as used herein generally refers to data that can be input into models, statistical models, algorithms and any system or process able to use existing data to make predictions. Training data can be normalized using the systems and methods described here.

As used herein, a "transition," may refer to or identify a peptide structure. In some embodiments, a transition can refer to the specific pair of m/z values associated with a precursor ion and a product or fragment ion.

III. Overview of Exemplary Workflow

FIG. 1 is a schematic diagram of an exemplary workflow 100 for the detection of peptide structures associated with a disease state for use in diagnosis and/or treatment in accordance with one or more embodiments. Workflow 100 may include various operations including, for example, sample collection 102, sample intake 104, sample preparation and processing 106, data analysis 108, and output generation 110.

Sample collection 102 may include, for example, obtaining a biological sample 112 of one or more subjects, such as subject 114. Biological sample 112 may take the form of a specimen obtained via one or more sampling methods. Biological sample 112 may be representative of subject 114 as a whole or of a specific tissue, cell type, or other category or sub-category of interest. Biological sample 112 may be obtained in any of a number of different ways. In various embodiments, biological sample 112 includes whole blood sample 116 obtained via a blood draw. In other embodiments, biological sample 112 includes set of aliquoted samples 118 that includes, for example, a serum sample, a plasma sample, a blood cell (e.g., white blood cell (WBC), red blood cell (RBC) sample, another type of sample, or a combination thereof. Biological samples 112 may include nucleotides (e.g. ssDNA, dsDNA, RNA), organelles, amino acids, peptides, proteins, carbohydrates, glycoproteins, or any combination thereof.

In various embodiments, a single run can analyze a sample comprising an external standard (e.g. NGEP), an internal standard, and a glycopeptide analyte. As such, abundance values (e.g. abundance or raw abundance) for external standard, internal standard, and target glycopeptide analyte can be determined by mass spectrometry in the same run.

In various embodiments, serum samples may be analyzed prior to analyzing experimental samples. In various embodiments, serum samples can be run independently between experimental samples. In some embodiments, serum samples can be analyzed after every 1, 2, 3, 4, 5, 6, 7, 8, 9, 10, 11, 12, 13, 14, 15, 16, 17, 18, 19, 20, or more experiments. In various embodiments, serum sample data can be used in some or all of the normalization systems and methods described herein. In additional embodiments, blank samples may be processed to prevent column fouling.

Sample intake 104 may include one or more various operations such as, for example, aliquoting, registering, processing, storing, thawing, and/or other types of operations. In one or more embodiments, when biological sample 112 includes whole blood sample 116, sample intake 104 includes aliquoting whole blood sample 116 to form a set of aliquoted samples that can then be sub-aliquoted to form set of samples 120.

Sample preparation and processing 106 may include, for example, one or more operations to form set of peptide structures 122. In various embodiments, set of peptide structures 122 may include various fragments of unfolded proteins that have undergone digestion and may be ready for analysis.

Further, sample preparation and processing 106 may include, for example, data acquisition 124 based on set of peptide structures 122. For example, data acquisition 124 may include use of, for example, but is not limited to, a liquid chromatography/mass spectrometry (LC/MS) system.

Data analysis 108 may include, for example, peptide structure analysis 126. In some embodiments, data analysis 108 also includes output generation 110. In other embodiments, output generation 110 may be considered a separate operation from data analysis 108. Output generation 110 may include, for example, generating final output 128 based on the results of peptide structure analysis 126. Final output 128 may be used for determining research, diagnosis, and/or treatment.

In various embodiments, final output 128 is comprised of one or more outputs. Final output 128 may take various forms. For example, final output 128 may be a report that includes, for example, a diagnosis output, a treatment output (e.g., a treatment design output, a treatment plan output, or combination thereof), analyzed data (e.g. relativized and normalized) or combination thereof. In some embodiments, report can comprise a target glycopeptide analyte concentration as a function of the NGEP concentration value and the normalized abundance value. In some embodiments, final output 128 may be an alert (e.g., a visual alert, an audible alert, etc.), a notification (e.g., a visual notification, an audible notification, an email notification, etc.), an email output, or a combination thereof. In some embodiments, final output 128 may be sent to remote system 130 for processing. Remote system 130 may include, for example, a computer system, a server, a processor, a cloud computing platform, cloud storage, a laptop, a tablet, a smartphone, some other type of mobile computing device, or a combination thereof.

In other embodiments, workflow 100 may optionally exclude one or more of the operations described herein and/or may optionally include one or more other steps or operations other than those described herein (e.g., in addition to and/or instead of those described herein). Accordingly, workflow 100 may be implemented in any of a number of different ways for use in the research, diagnosis, and/or treatment of a disease state.

IV. Detection and Quantification of Peptide Structures

Figure 2A:
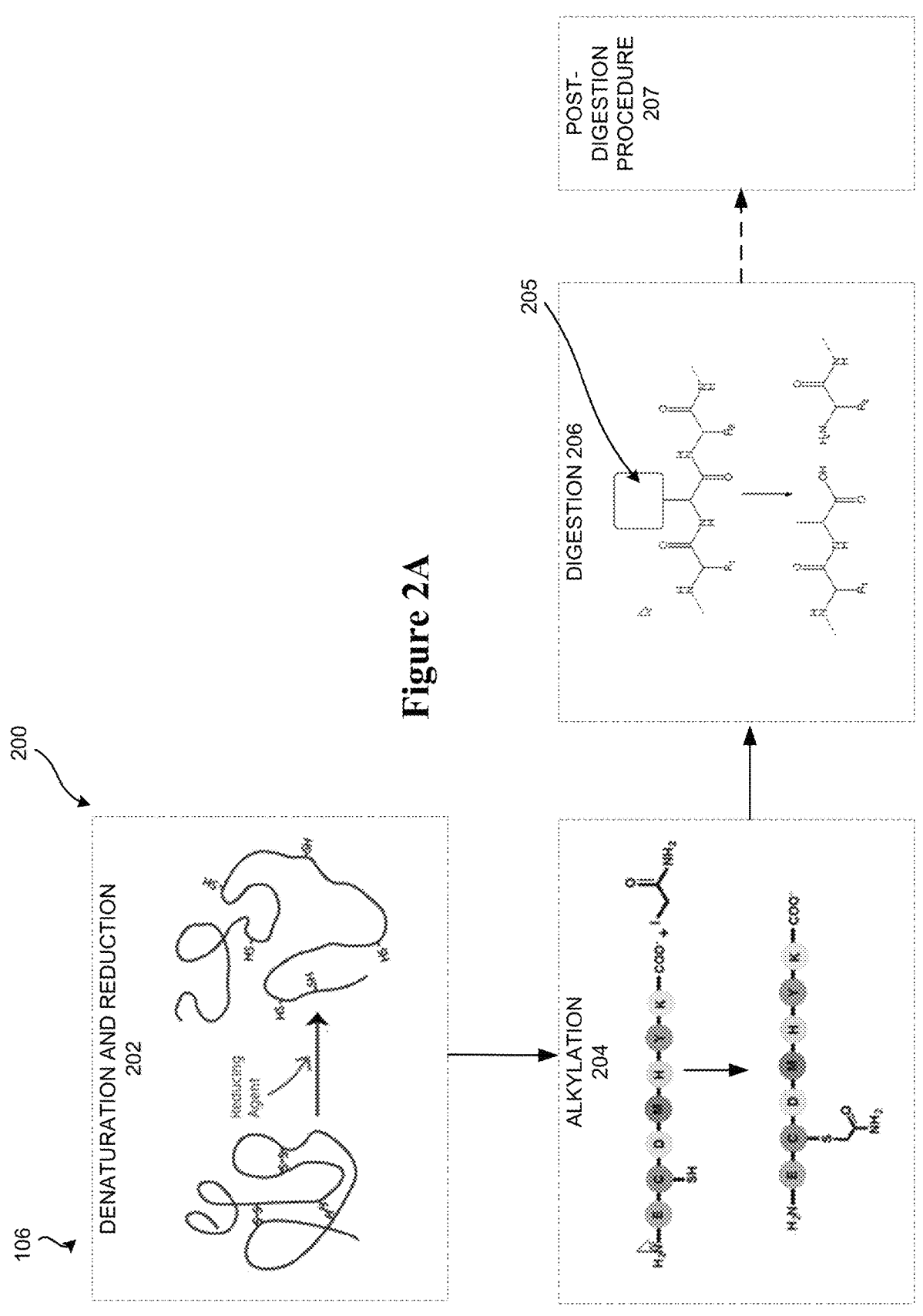
FIG. 2A is a schematic diagram of a preparation workflow in accordance with one or more embodiments.
Figure 2B:
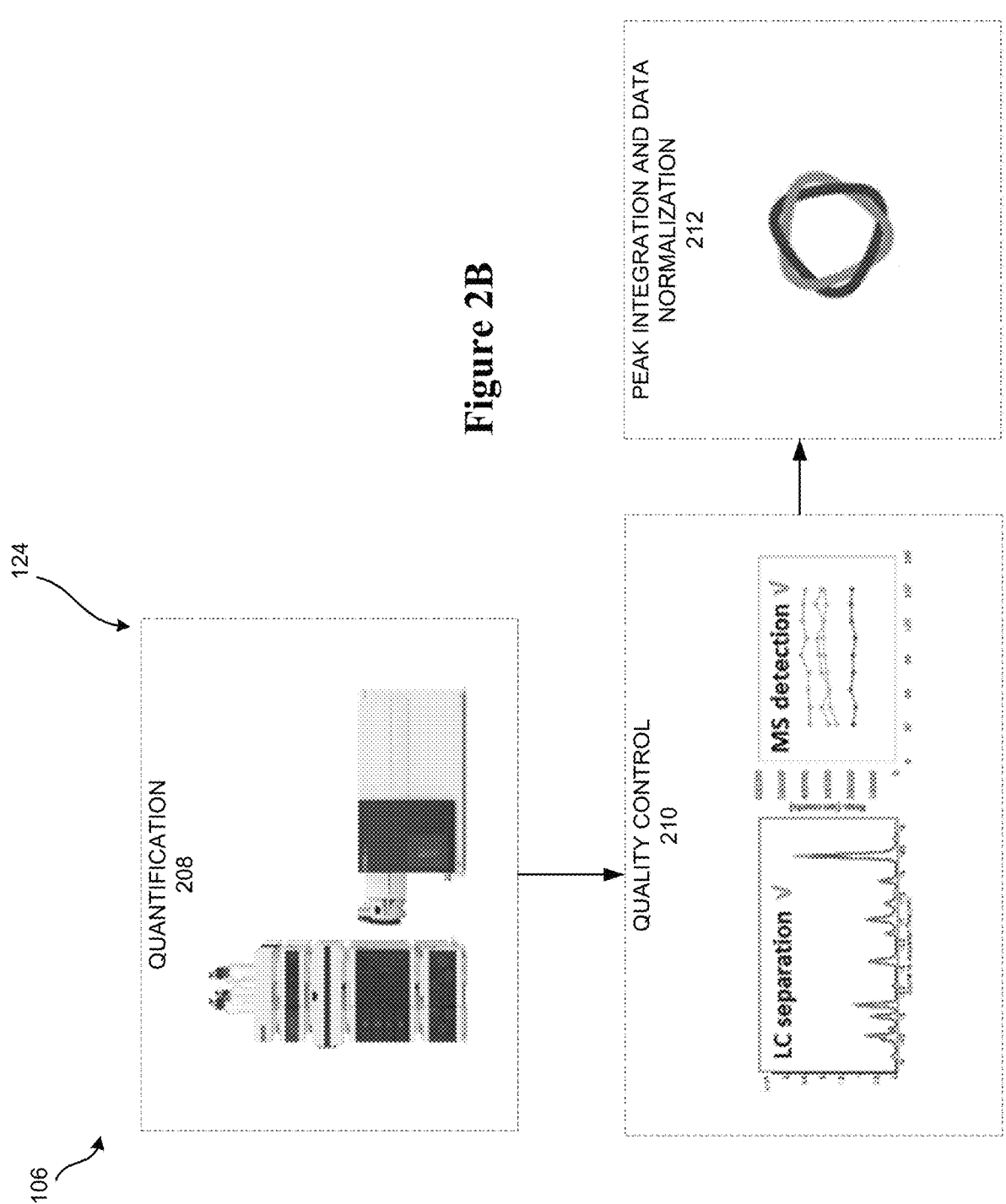
FIG. 2B is a schematic diagram of data acquisition in accordance with one or more embodiments.

FIGS. 2A and 2B are schematic diagrams of a workflow for sample preparation and processing 106 in accordance with one or more embodiments. FIGS. 2A and 2B are described with continuing reference to FIG. 1. Sample preparation and processing 106 may include, for example, preparation workflow 200 shown in FIG. 2A and data acquisition 124 shown in FIG. 2B.

IV.A. Sample Preparation and Processing

FIG. 2A is a schematic diagram of preparation workflow 200 in accordance with one or more embodiments. Preparation workflow 200 may be used to prepare a sample, such as a sample of set of samples 120 in FIG. 1, for analysis via data acquisition 124. For example, this analysis may be performed via mass spectrometry (e.g. LC-MS). In various embodiments, preparation workflow 200 may include denaturation and reduction 202, alkylation 204, and digestion 206. All areas of the preparation workflow can cause inconsistency between different samples and different experiments, necessitating, the improved normalization systems and methods described herein and throughout.

In general, polymers, such as proteins, in their native form, can fold to include secondary, tertiary, and/or other higher order structures. Such higher order structures may functionalize proteins to complete tasks (e.g. enable enzymatic activity) in a subject. Further, such higher order structures of polymers may be maintained via various interactions between side chains of amino acids within the polymers. Such interactions can include ionic bonding, hydrophobic interactions, hydrogen bonding, and disulfide linkages between cysteine residues. However, when using analytic systems and methods, including mass spectrometry, unfolding such polymers (e.g. peptide/protein molecules) may be desired to obtain sequence information. In some embodiments, unfolding a polymer may include denaturing the polymer, which may include, for example, linearizing the polymer.

In one or more embodiments, denaturation and reduction 202 can be used to disrupt higher order structures (e.g., secondary, tertiary, quaternary, etc.) of one or more proteins (e.g., polypeptides and peptides) in a sample (e.g., one of set of samples 120 in FIG. 1). Denaturation and reduction 202 includes, for example, a denaturation procedure and a reduction procedure. In some embodiments, the denaturation procedure may be performed using, for example, thermal denaturation, where heat is used as a denaturing agent. The thermal denaturation can disrupt ionic bonding, hydrophobic interactions, and/or hydrogen bonding.

In one or more embodiments, the denaturation procedure may include using one or more denaturing agents in combination with heat. These one or more denaturing agents may include, for example, but are not limited to, any number of chaotropic salts (e.g., urea, guanidine), surfactants (e.g., sodium dodecyl sulfate (SDS), beta octyl glucoside, Triton X-100), or combination thereof. In some cases, such denaturing agents may be used in combination with heat when sample preparation workflow further includes a cleanup procedure.

The resulting one or more denatured (e.g., unfolded, linearized) proteins may then undergo further processing in preparation of analysis. For example, a reduction procedure may be performed in which one or more reducing agents are applied. A reducing agent may take the form of, for example, without limitation, dithiothreitol (DTT), tris(2-carboxyethyl)phosphine (TCEP), or some other reducing agent. The reducing agent may reduce (e.g., cleave) the disulfide linkages between cysteine residues of the one or more denatured proteins to form one or more reduced proteins.

In various embodiments, the one or more reduced proteins resulting from denaturation and reduction 202 may undergo a process to prevent the reformation of disulfide linkages between, for example, the cysteine residues of the one or more reduced proteins. This process may be implemented using alkylation 204 to form one or more alkylated proteins. For example, alkylation 204 may be used add an acetamide group to a sulfur on each cysteine residue to prevent disulfide linkages from reforming. In various embodiments, an acetamide group can be added by reacting one or more alkylating agents with a reduced protein. The one or more alkylating agents may include, for example, one or more acetamide salts. An alkylating agent may take the form of, for example, iodoacetamide (IAA), 2-chloroacetamide, some other type of acetamide salt, or some other type of alkylating agent.

In some embodiments, alkylation 204 may include a quenching procedure. The quenching procedure may be performed using one or more reducing agents (e.g., one or more of the reducing agents described above).

In various embodiments, the one or more alkylated formed via alkylation 204 can then undergo digestion 206 in preparation for analysis (e.g., mass spectrometry analysis). Digestion 206 of a protein may include cleaving the protein at or around one or more cleavage sites (e.g., site 205 which may be one or more amino acid residues). For example, without limitation, an alkylated protein may be cleaved at the carboxyl side of the lysine or arginine residues. This type of cleavage may break the protein into various segments, which include one or more peptide structures (e.g., glycosylated or aglycosylated).

In various embodiments, digestion 206 is performed using one or more proteolysis catalysts. For example, an enzyme can be used in digestion 206. In some embodiments, the enzyme takes the form of trypsin. In other embodiments, one or more other types of enzymes (e.g., proteases) may be used in addition to or in place of trypsin. These one or more other enzymes include, but are not limited to, LysC, LysN, AspN, GluC, and ArgC. In some embodiments, digestion 206 may be performed using tosyl phenylalanyl chloromethyl ketone (TPCK)-treated trypsin, one or more engineered forms of trypsin, one or more other formulations of trypsin, or a combination thereof. In some embodiments, digestion 206 may be performed in multiple steps, with each involving the use of one or more digestion agents. For example, a secondary digestion, tertiary digestion, etc. may be performed. In one or more embodiments, trypsin is used to digest serum samples. In one or more embodiments, trypsin/LysC cocktails are used to digest plasma samples.

In some embodiments, digestion 206 further includes a quenching procedure. The quenching procedure may be performed by acidifying the sample (e.g., to a pH<3). In some embodiments, formic acid may be used to perform this acidification.

In various embodiments, preparation workflow 200 further includes post-digestion procedure 207. Post-digestion procedure 207 may include, for example, a cleanup procedure. The cleanup procedure may include, for example, the removal of unwanted components in the sample that results from digestion 206. For example, unwanted components may include, but are not limited to, inorganic ions, surfactants, etc. In some embodiments, post-digestion procedure 207 further includes a procedure for the addition of heavy-labeled peptide internal standards.

Although preparation workflow 200 has been described with respect to a sample created or taken from biological sample 112 that is blood-based (e.g., a whole blood sample, a plasma sample, a serum sample, etc.), sample preparation workflow 200 may be similarly implemented for other types of samples (e.g., tears, urine, tissue, interstitial fluids, sputum, etc.) to produce set of peptides structures 122.

IV.B. Peptide Structure Identification and Quantitation

FIG. 2B is a schematic diagram of data acquisition 124 in accordance with one or more embodiments. In various embodiments, data acquisition 124 can commence following sample preparation 200 described in FIG. 2A. In various embodiments, data acquisition 124 can comprise quantification 208, quality control 210, and peak integration and normalization 212.

In various embodiments, targeted quantification 208 of peptides and glycopeptides can incorporate use of liquid chromatography-mass spectrometry LC/MS instrumentation. For example, LC-MS/MS, or tandem MS may be used. In general, LC/MS (e.g., LC-MS/MS) can combine the physical separation capabilities of liquid chromatograph (LC) with the mass analysis capabilities of mass spectrometry (MS). According to some embodiments described herein, this technique allows for the separation of digested peptides to be fed from the LC column into the MS ion source through an interface.

In various embodiments, any LC/MS device can be incorporated into the workflow described herein. In various embodiments, a Triple Quadrupole LC/MS™ includes example instruments suited for identification and targeted quantification 208. In various embodiments, targeted quantification 208 is performed using multiple reaction monitoring mass spectrometry (MRM-MS).

In various embodiments described herein, identification of a particular protein or peptide and an associated quantity can be assessed. In various embodiments described herein, identification of a particular glycan and an associated quantity can be assessed. In various embodiments described herein, particular glycans can be matched to a glycosylation site on a protein or peptide and the abundance values measured.

In some cases, targeted quantification 208 includes using a specific collision energy associated for the appropriate fragmentation to consistently see an abundant product ion. Glycopeptide structures may have a lower collision energy than aglycosylated peptide structures. When analyzing a sample that includes glycopeptide structures, the source voltage and gas temperature may be lowered as compared to generic proteomic analysis.

In various embodiments, quality control 210 procedures can be put in place to optimize data quality. In various embodiments, measures can be put in place allowing only errors within acceptable ranges outside of an expected value. In various embodiments, employing statistical models (e.g. using Westgard rules) can assist in quality control 210. For example, quality control 210 may include, for example, assessing the retention time and abundance of representative peptide structures (e.g., glycosylated and/or aglycosylated) and spiked-in internal standards, in either every sample, or in each quality control sample (e.g., pooled serum digest).

Peak integration and normalization 212 may be performed to process the data that has been generated and transform the data into a format for analysis. For example, peak integration and normalization 212 may include converting abundance data for various product ions that were detected for a selected peptide structure into a single quantification metric (e.g., a relative quantity, an adjusted quantity, a normalized quantity, a relative concentration, an adjusted concentration, a normalized concentration, etc.) for that peptide structure. In some embodiments, peak integration and normalization 212 may be performed using one or more of the techniques described in U.S. Patent Publication No. 2020/0372973A1 and/or US Patent Publication No. 2020/0240996A1, the disclosures of which are incorporated by reference herein in their entireties.

V. Peptide Structure Data Analysis

Figure 3:
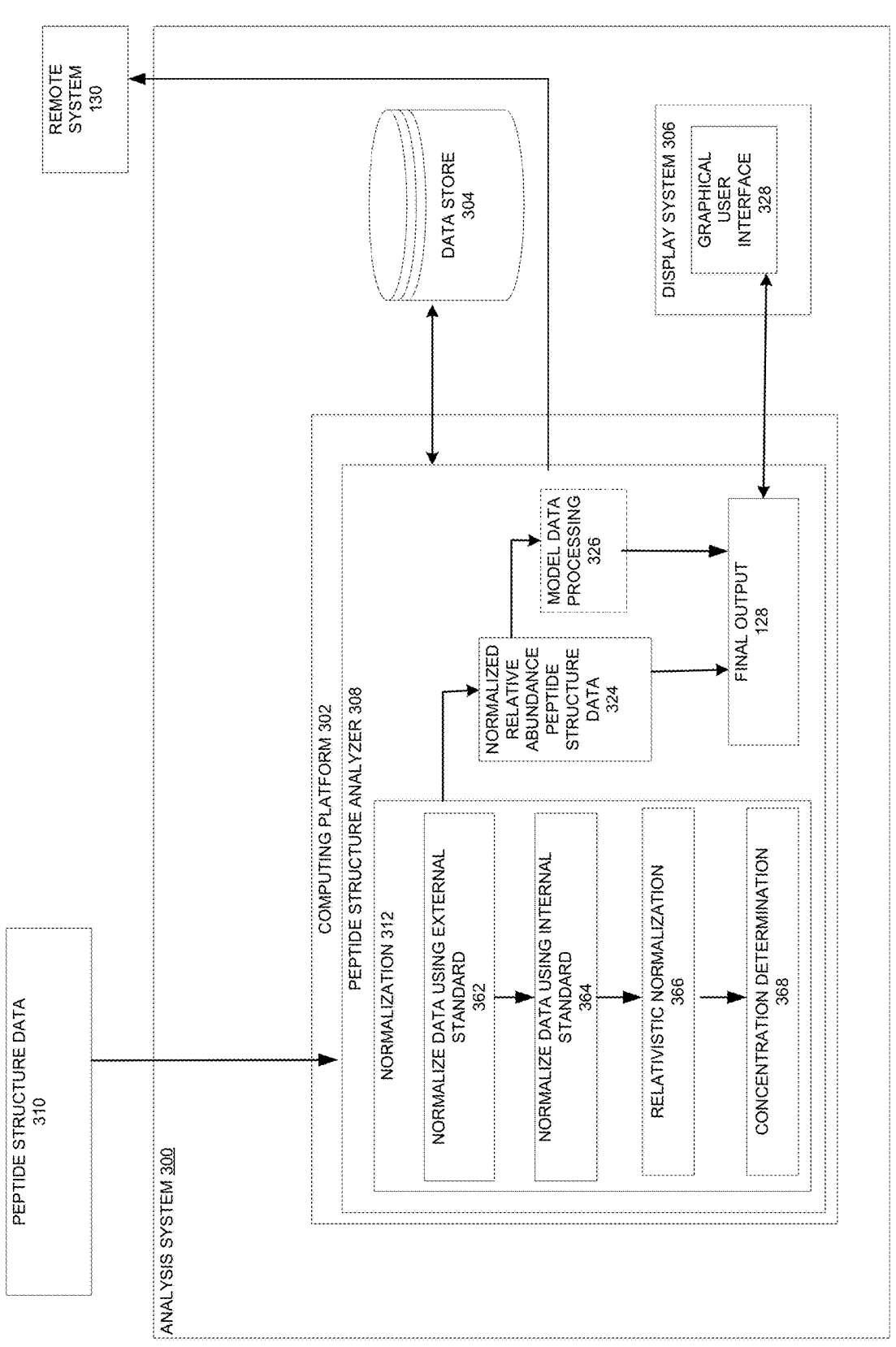
FIG. 3 is a block diagram of an analysis system in accordance with one or more embodiments.

V.A. Exemplary System for Peptide Structure Data Analysis
V.A.1. Analysis System for Peptide Structure Data Analysis FIG. 3 is a block diagram of an analysis system 300 in accordance with one or more embodiments. Analysis system 300 may be used, for example, to both detect and analyze various peptide structures that have been associated to various disease states. Analysis system 300 is one example of an implementation for a system that may be used to perform data analysis 108 in FIG. 1. Thus, analysis system 300 is described with continuing reference to workflow 100 as described in FIGS. 1, 2A, and/or 2B.

Analysis system 300 may include computing platform 302 and data store 304. In some embodiments, analysis system 300 also includes display system 306. Computing platform 302 may take various forms. In one or more embodiments, computing platform 302 includes a single computer (or computer system) or multiple computers in communication with each other. In other examples, computing platform 302 takes the form of a cloud computing platform.

Data store 304 and display system 306 may each be in communication with computing platform 302. In some examples, data store 304, display system 306, or both may be considered part of or otherwise integrated with computing platform 302. Thus, in some examples, computing platform 302, data store 304, and display system 306 may be separate components in communication with each other, but in other examples, some combination of these components may be integrated together. Communication between these different components may be implemented using any number of wired communications links, wireless communications links, optical communications links, or a combination thereof.

Analysis system 300 includes, for example, peptide structure analyzer 308, which may be implemented using hardware, software, firmware, or a combination thereof. In one or more embodiments, peptide structure analyzer 308 is implemented using computing platform 302.

Peptide structure analyzer 308 receives peptide structure data 310 (e.g. abundance values for a transition) for processing. Peptide structure data 310 may be, for example, the peptide structure data that is output from sample preparation and processing 106 in FIGS. 1, 2A, and 2B. Peptide structure data 310 may correspond to set of peptide structures 122 identified for biological sample 112 and may thereby correspond to biological sample 112. In some embodiments, biological sample 112 can comprise a biological sample obtained from a subject. In some embodiments, biological sample 112 can comprise an internal standard. In some embodiments, biological sample 112 can comprise an external standard.

Peptide structure data 310 may comprise a set of quantification values for each peptide structure of a plurality of peptide structures. In various embodiments, quantification values may comprise raw data received from a mass spectrometry instrument. Raw data may comprise a mass to charge ratio identifying a peptide structure and a raw abundance for an analyte (e.g. a peptide structure). In various embodiments, relative abundance can be determined from raw abundances. Quantification data for a peptide structures take the form of any of the following prior to, during, and post analysis from one of a relative quantity, an adjusted quantity, and a normalized quantity. In this manner, peptide structure data 310 may provide abundance information about the plurality of peptide structures with respect to biological sample 112.

In some embodiments, a peptide structure of set of peptide structures comprises a glycosylated peptide structure, or glycopeptide structure, that is defined by a peptide sequence and a glycan structure attached to a linking site of the peptide sequence quantity. For example, the peptide structure may be a glycopeptide or a portion of a glycopeptide. In some embodiments, a peptide structure of set of peptide structures 318 comprises an aglycosylated or non-glycosylated peptide structure that is defined by a peptide sequence. For example, the peptide structure may be a peptide or a portion of a peptide and may be referred to as a quantification peptide.

Peptide structure data 310 can be sent as input into peptide structure analyzer 308, retrieved from data store 304 or some other type of storage (e.g., cloud storage), accessed from cloud storage, or obtained in some other manner. In some cases, peptide structure data 310 may be retrieved from data store 304 in response to (e.g., directly or indirectly based on) receiving user input entered by a user via an input device.

Peptide structure analyzer 308 may receive peptide structure data 310 for processing. Received peptide structure data 310 by the peptide structure analyzer 308 may comprise raw abundance data from peptide structures (e.g., raw abundance data for glycopeptide analytes, glycopeptide target analytes external standards, and/or internal standards). As such, peptide structure analyzer 308 may further process peptide structure data 310 using, for example, a normalization module for performing normalization 312 to generate normalized peptide structure data. Normalization 312 may be implemented in any of a number of different ways and may include number of or combination of steps. Normalization 312 may be implemented using any number of models, functions, equations, algorithms, and/or other mathematical techniques. The present disclosure comprises novel systems and methods for normalizing peptide structure data 310 within an individual sample and across experiments.

In one or more embodiments, normalization 312 includes various steps such as, for example, normalize data using external standard 362, normalize data using internal standard 364, relativistic normalization 366, and concentration determination 368. Aspects of normalization 312 can be carried out by inputting peptide structure data 310 into peptide structure analyzer 308. Normalization 312 of peptide structure analyzer 308 can process peptide structure data using steps 362, 364, and 366. Processed peptide structure data can be used as input for concentration determination 368. In various embodiments, concentration determination 368 occurs as a last step.

In various aspects, the processes in normalization 312 can be executed to generate normalized relative abundance peptide structure data 324 from the peptide structure data 310. Peptide structure analyzer 308 may generate final output 128 based on normalized relative abundance peptide structure data 324. In other embodiments, final output 128 may be an output including normalized abundance data, normalized relative abundance peptide structure data, and/or may include data that has undergone model data processing 326. In other embodiments, final output 128 may be an output generated by normalization 312 and model data processing 326. Model data processing 326 may be performed to train a model and/or use a trained model for diagnosing a disease state.

For example, the normalized relative abundance peptide structure data 324 can be generated in a form suitable for model data processing 326. In some embodiments, normalized relative abundance peptide structure data 324 may include concentration values for peptide structures (e.g. target glycopeptide analyte concentrations) that can be comparable with respect to concentrations across multiple experiments.

In various embodiments, model data processing 326 may include, but is not limited to, at least one of a parametric model, a non-parametric model, deep learning model, a neural network, a linear discriminant analysis model, a quadratic discriminant analysis model, a support vector machine, a random forest algorithm, a nearest neighbor algorithm (e.g., a k-Nearest Neighbors algorithm), a combined discriminant analysis model, a k-means clustering algorithm, an unsupervised model, a multivariable regression model, a penalized multivariable regression model, or another type of model.

Aspects of training predictive models, such as the ones listed above, may rely heavily on inputting large quantities of high-quality training data. In order to use large quantities of data, the data must first be made comparable across samples both within the same experiment and across different experiments. This can include accounting for contributors of variation in sample preparation, analysis, experimental conditions, and changes of conditions between experiment runs. Making and improving data comparison can be done using the systems and methods described herein and throughout.

V.A.2. Computer Implemented System

Figure 4:
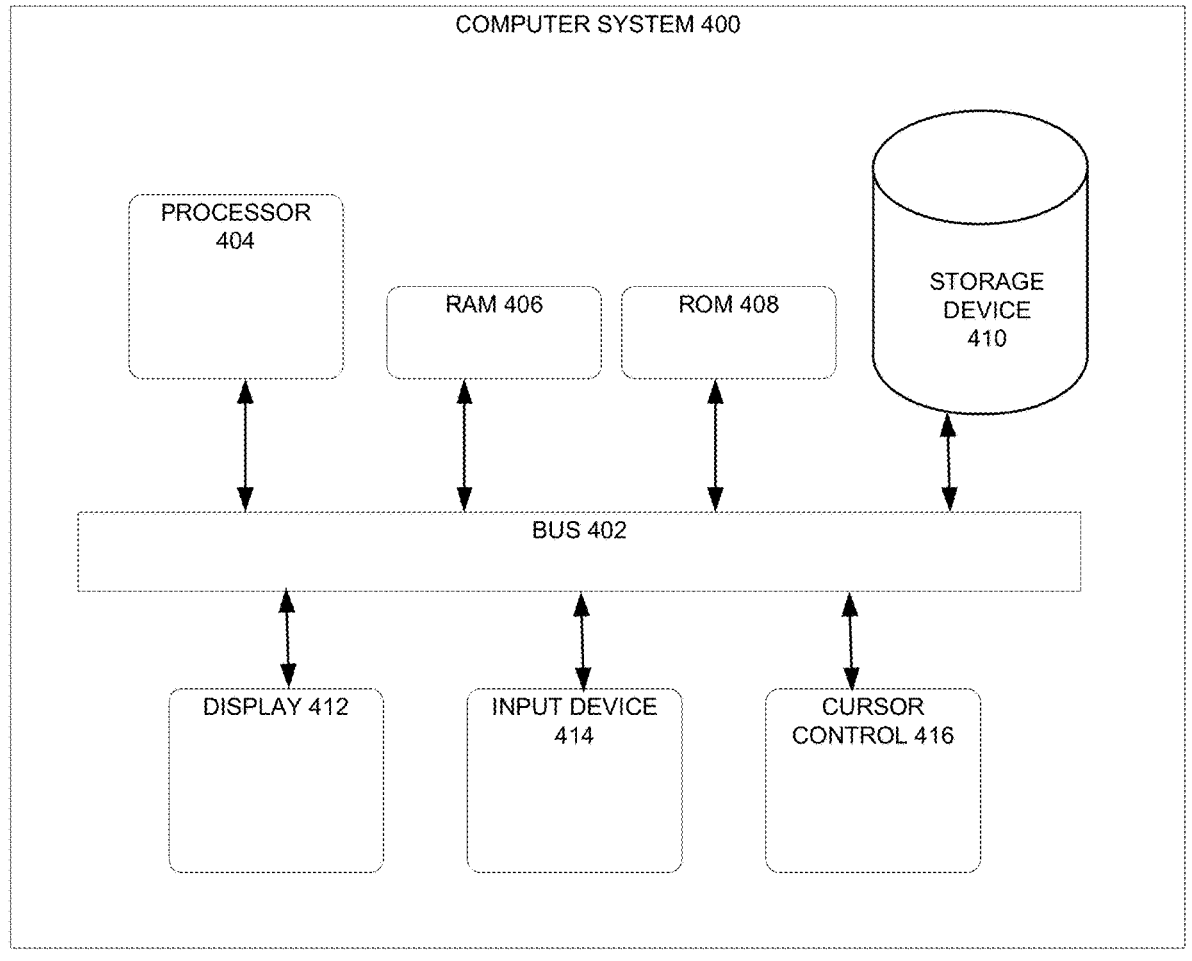
FIG. 4 is a block diagram of a computer system in accordance with various embodiments.

FIG. 4 is a block diagram of a computer system in accordance with various embodiments. Computer system 400 may be an example of one implementation for computing platform 302 described above in FIG. 3 and/or one or more systems in FIG. 14.

In one or more examples, computer system 400 can include a bus 402 or other communication mechanism for communicating information, and a processor 404 coupled with bus 402 for processing information. In various embodiments, computer system 400 can also include a memory, which can be a random-access memory (RAM) 406 or other dynamic storage device, coupled to bus 402 for determining instructions to be executed by processor 404. Memory also can be used for storing temporary variables or other intermediate information during execution of instructions to be executed by processor 404. In various embodiments, computer system 400 can further include a read only memory (ROM) 408 or other static storage device coupled to bus 402 for storing static information and instructions for processor 404. A storage device 410, such as a magnetic disk or optical disk, can be provided and coupled to bus 402 for storing information and instructions.

In various embodiments, computer system 400 can be coupled via bus 402 to a display 412, such as a cathode ray tube (CRT) or liquid crystal display (LCD), for displaying information to a computer user. An input device 414, including alphanumeric and other keys, can be coupled to bus 402 for communicating information and command selections to processor 404. Another type of user input device is a cursor control 416, such as a mouse, a joystick, a trackball, a gesture input device, a gaze-based input device, or cursor direction keys for communicating direction information and command selections to processor 404 and for controlling cursor movement on display 412. This input device 414 typically has two degrees of freedom in two axes, a first axis (e.g., x) and a second axis (e.g., y), that allows the device to specify positions in a plane. However, it should be understood that input devices 414 allowing for three-dimensional (e.g., x, y, and z) cursor movement are also contemplated herein.

Consistent with certain implementations of the present teachings, results can be provided by computer system 400 in response to processor 404 executing one or more sequences of one or more instructions contained in RAM 406. Such instructions can be read into RAM 406 from another computer-readable medium or computer-readable storage medium, such as storage device 410. Execution of the sequences of instructions contained in RAM 406 can cause processor 404 to perform the processes described herein. Alternatively, hard-wired circuitry can be used in place of or in combination with software instructions to implement the present teachings. Thus, implementations of the present teachings are not limited to any specific combination of hardware circuitry and software.

The term "computer-readable medium" (e.g., data store, data storage, storage device, data storage device, etc.) or "computer-readable storage medium" as used herein refers to any media that participates in providing instructions to processor 404 for execution. Such a medium can take many forms, including but not limited to, non-volatile media, volatile media, and transmission media. Examples of non-volatile media can include, but are not limited to, optical, solid state, magnetic disks, such as storage device 410. Examples of volatile media can include, but are not limited to, dynamic memory, such as RAM 406. Examples of transmission media can include, but are not limited to, coaxial cables, copper wire, and fiber optics, including the wires that comprise bus 402.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, or any other tangible medium from which a computer can read.

In addition to computer readable medium, instructions or data can be provided as signals on transmission media included in a communications apparatus or system to provide sequences of one or more instructions to processor 404 of computer system 400 for execution. For example, a communication apparatus may include a transceiver having signals indicative of instructions and data. The instructions and data are configured to cause one or more processors to implement the functions outlined in the disclosure herein. Representative examples of data communications transmission connections can include, but are not limited to, telephone modem connections, wide area networks (WAN), local area networks (LAN), infrared data connections, NFC connections, optical communications connections, etc.

It should be appreciated that the methodologies described herein, flow charts, diagrams, and accompanying disclosure can be implemented using computer system 400 as a stand-alone device or on a distributed network of shared computer processing resources such as a cloud computing network.

The methodologies described herein may be implemented by various means depending upon the application. For example, these methodologies may be implemented in hardware, firmware, software, or any combination thereof. For a hardware implementation, the processing unit may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, electronic devices, other electronic units designed to perform the functions described herein, or a combination thereof.

In various embodiments, the methods of the present teachings may be implemented as firmware and/or a software program and applications written in conventional programming languages such as C, C++, Python, etc. If implemented as firmware and/or software, the embodiments described herein can be implemented on a non-transitory computer-readable medium in which a program is stored for causing a computer to perform the methods described above. It should be understood that the various engines described herein can be provided on a computer system, such as computer system 400, whereby processor 404 would execute the analyses and determinations provided by these engines, subject to instructions provided by any one of, or a combination of, the memory components RAM 406, ROM, 408, or storage device 410 and user input provided via input device 414.

VI. Exemplary Normalization Approaches

In various aspects of data collection, glycopeptide abundance readouts in targeted LC-MS experiments vary from run to run or experiment to experiment, or even for the same sample, based on digestion efficiency, ionization efficiency, detector sensitivity, run order effects, and other issues. The normalization methods below and throughout can correct for these and other issues.

Aspects of the disclosure include systems and methods for comparing data across multiple samples and experiments. In various embodiments, an initial step can include determining a corrected abundance using external standards. In various embodiments, another step can include determining non-glycosylated peptide concentrations using internal standards. In various embodiments, another step can include determining normalized/relative abundance of a glycopeptide analyte. In various embodiments, a final step can include determining concentration of a peptide analyte by multiplying the normalized/relative abundance value by the non-glycosylated endogenous peptide concentration. In various embodiments, the determining concentration step must occur subsequently to the previously listed steps.

VI.A. Normalize Data Using External Standard

Aspects of the disclosure can comprise determining for a corrected abundance for an individual transition (e.g. a non-glycosylated endogenous peptide [NGEP]) using a single-point calibration to an external standard.

Non-limiting examples of external standards can comprise pooled serum sample digest (e.g. pooled serum digest if biological samples to be analyzed is serum; pooled plasma digest if biological samples to be analyzed is plasma).

In various embodiments, when using pooled sample serum (e.g. Sigma Serum), markers can be selected that can be known to be present in the serum reference standard and the abundance differences can be used to align all abundance values of that marker in individual runs. In various embodiments, this can be done for any number of transitions. In some embodiments, there can be one transition per biomarker. In other embodiments, there can be one or more transitions per biomarker.

In various embodiments, two flanking pooled serum standard relative abundances can be used for a given marker (e.g. glycopeptide analyte).

Figure 8A:
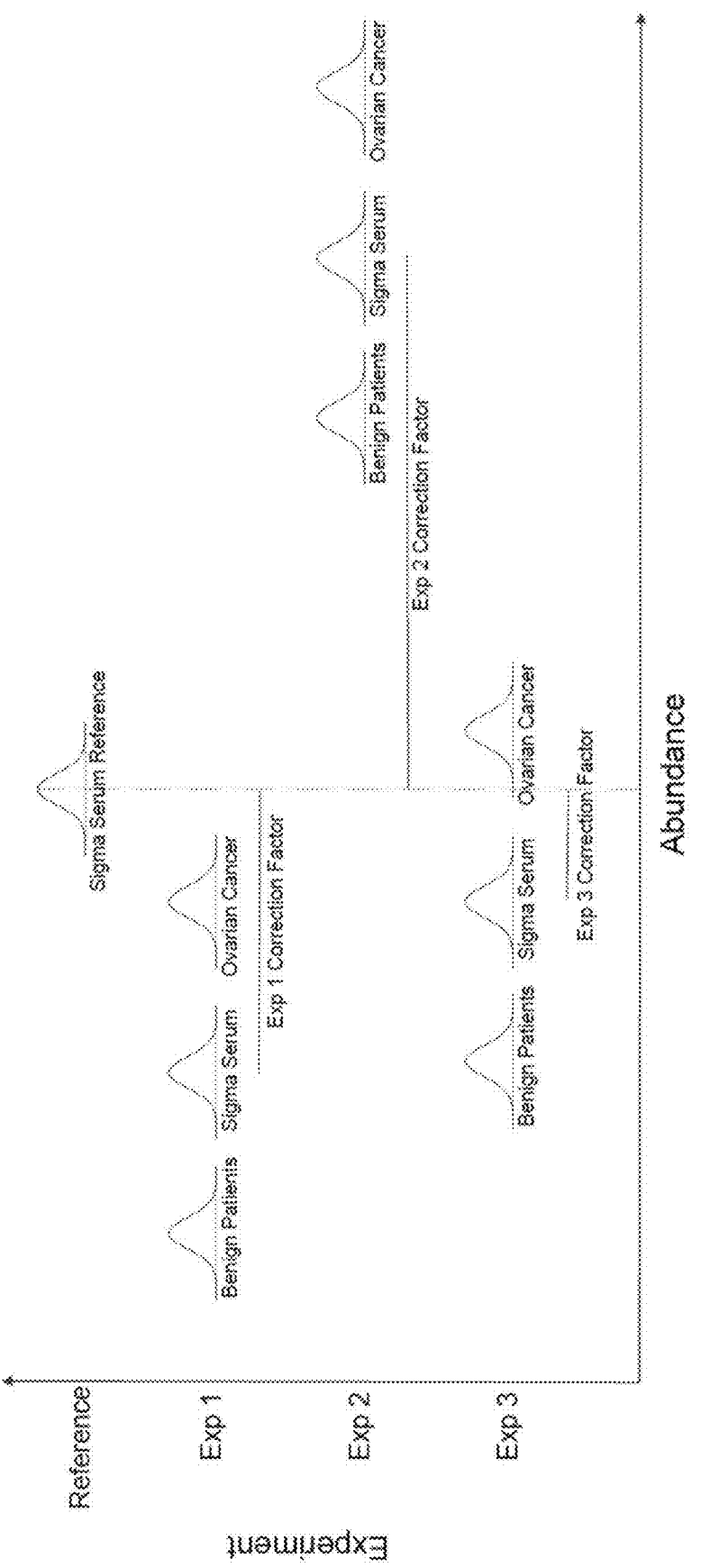
FIG. 8A illustrates hypothetical abundance values for three experiments prior to applying normalization methods described below and herein according to various embodiments.
Figure 8B:
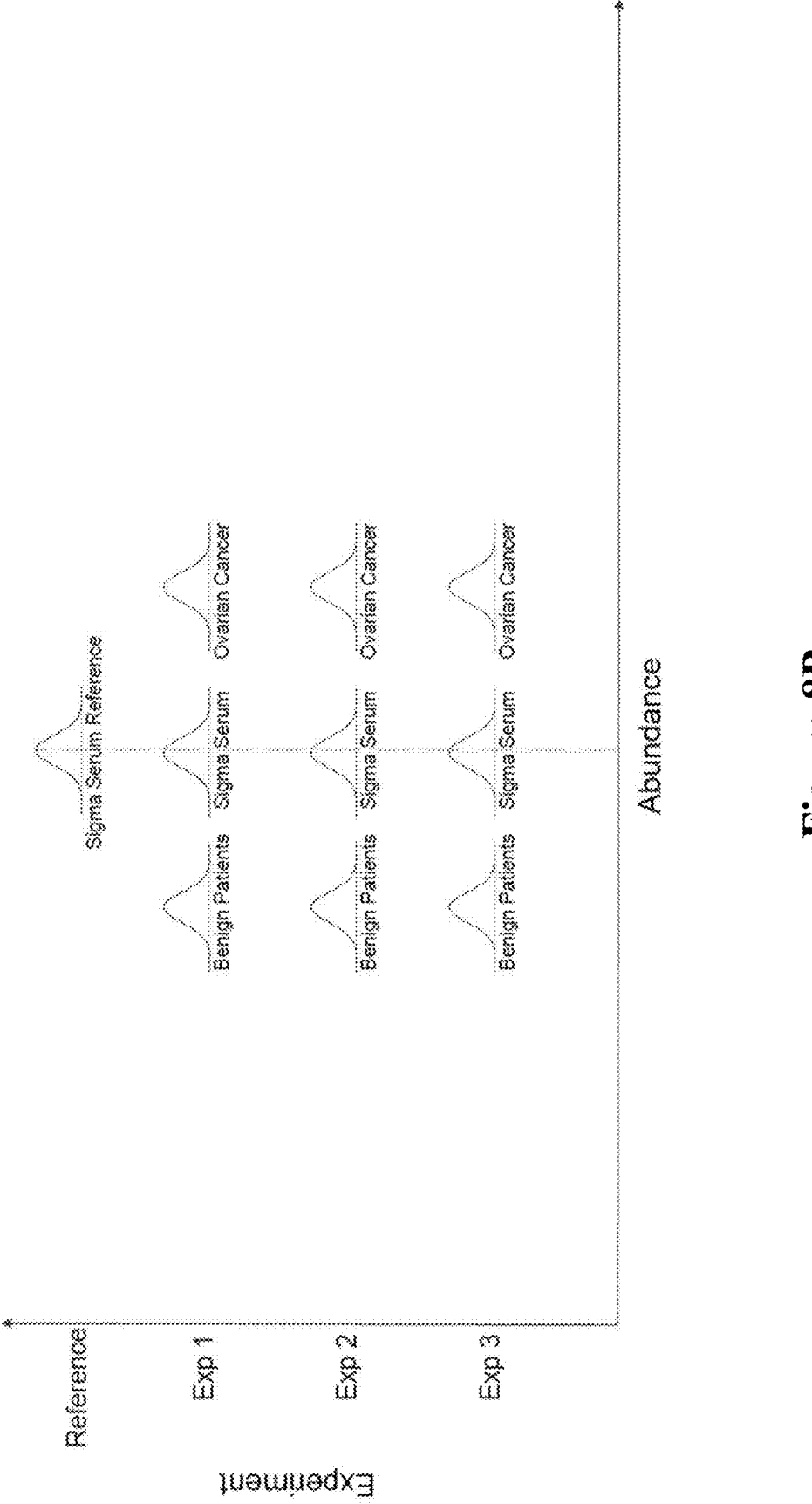
FIG. 8B illustrates hypothetical abundance values for three experiments after applying normalization methods described below and herein according to various embodiments.

Referring to FIG. 8A, hypothetical abundance values for three experiments are shown graphically prior to applying the normalize data using external standards methods described above and herein according to various embodiments. Referring to FIG. 8B, hypothetical abundance values for three experiments are shown graphically after applying the normalization methods described below and herein according to various embodiments. As illustrated, experimental data can be processed so as to allow for better comparisons across experiments in accordance with various embodiments.

VI.B. Normalize Data Using Internal Standard

In various embodiments, the following determination can be used in conjunction with use of internal standards. Internal standards can be useful for normalizing abundance values for a given sample. In some embodiments, internal standards can be "spiked-in" to each sample at specified, known concentrations and volumes. Internal standards can be effective in cases where enough is used to rise above a detection threshold (e.g. they can be detected). Non-glycosylated endogenous peptide (NGEP) concentration=(corrected non-glycosylated endogenous peptide abundance/ measured internal standard abundance)*known internal standard concentration.

In various embodiments, an NGEP concentration can later be used in calculating a concentration of a glycopeptide analyte. At least one internal standard per protein being analyzed can be measured in accordance with various embodiments.

In various embodiments, an internal standard can comprise a known concentration of a synthetic peptide corresponding to a given protein. In some embodiments, use of the synthetic non-glycosylated peptide standards can generate a cost savings because glycosylated standards can be both difficult to come by and can be costly. In various embodiments, internal standards can comprise heavy-labeled peptides of a glycopeptide analyte target of an MRM-MS list. Alternatively, internal standards can comprise non-heavy labeled standards.

In some embodiments, internal standards can comprise fewer peptides than are being analyzed. Therefore, if an internal standard peptide is not available for each peptide for reach glycoprotein, other internal standards can be selected as a "surrogate" internal standard based on similarity. In some embodiments, similarity comprises an m/z comparison. In other embodiments, similarity comprises an RT comparison.

VI.C. Relativistic Normalization

Aspects of the disclosure can be directed toward measuring an abundance of a glycopeptide analyte and determining a frequency of the glycopeptide analyte in accordance with various embodiments. In some embodiments, the frequency can comprise a relativistic normalization value. In some embodiments, the relativistic normalization value can include the ratio of a measured abundance of a glycopeptide analyte (e.g. a glycoform) divided by a normalization factor (e.g. peptide abundance or a site occupancy total). In some embodiments, the determination can be based on making a comparison of the glycopeptide analyte to a non-glycosylated peptide from the same protein (e.g. peptide abundance comparison). In some embodiments, the determination can be based on making a comparison of the glycopeptide analyte abundance to an abundance of other glycoforms at the same glycosylation site (e.g. a site occupancy total).

In various embodiments, using a relative abundance approach (e.g. a comparison of the glycopeptide analyte to a non-glycosylated peptide from the same protein) to relativistic normalization may be used when two or less glycoforms exist for a given glycosylation site. In various embodiments, using a site occupancy abundance approach (e.g. a comparison of the glycopeptide analyte abundance to an abundance of other glycoforms at the same glycosylation site) to relativistic normalization may be used when three or more glycoforms exist for a given glycosylation site.

In various embodiments, relativistic normalization can be or produce a value comprising information relating to what fraction a particular glycoform (e.g. glycopeptide analyte) occurs relative to a total of all glycoforms for a given glycosylation site. In some embodiments, the value can comprise a percentage. In some embodiments, the value can comprise a fraction. In some embodiments, the value can comprise an abundance value for a glycopeptide analyte accounting for abundance values of all glycoforms of a peptide.

VI.C.1.Relative Abundance

Aspects of the disclosure consider and correct for variation generated within a single experiment such as well-to-well variation, patient to patient, and run order.

In various aspects, normalized-relative abundance of a glycopeptide analyte can be determined by dividing the measured abundance of the target glycopeptide analyte (e.g. a glycoform) by the measured abundance of a non-glycosylated peptide of the same protein. As previously stated, a relative abundance can be calculated as a measured abundance value for a glycoform (e.g. a glycopeptide or a maker) divided by a corresponding quantification peptide abundance for various embodiments. For a hypothetical example, (glycopeptide abundance 3000)/(quantification peptide abundance for another non-glycosylated peptide of the same protein 30000)=10% glycosylation.

In some embodiments, an advantage of the relative abundance approach can be that it may account for any kind of glycopeptide no matter how many glycans/glycan sites exist or are measured for a given glycoprotein or peptide.

VI.C.2.Site Occupancy Abundance

In various embodiments, a site occupancy approach can be used in determining relativistic abundance. In various embodiments, a site occupancy approach can comprise determining a per-site glycopeptide occupancy proportion across all glycan observed at that site. In some embodiments, such an approach can be more effective when more than one glycoform is present on site. In some embodiments, abundance values can be measured for each glycoform and then totaled. A relativistic abundance value can then be determined by dividing an abundance value for a single glycoform by the total abundances of all glycoforms for a given glycosylation site. For a hypothetical example, (glycoform 1 abundance) can be divided by (glycoform 1 abundance+glycoform 2 abundance+glycoform 3 abundance)

In various embodiments, the site occupancy approach can account for ionization efficiencies across glycopeptides.

In various embodiments, instead of using site occupancy for a given protein, a sum of abundances of all quantification peptides for a given subject can be used.

VI.D. Concentration Determination

In various embodiments, a final step can be completed to obtain an approximate concentration of a glycopeptide analyte. In various embodiments an approximate concentration of a glycopeptide analyte can be determined by multiplying the normalized (relative) abundance value or site occupancy abundance value, as appropriately obtained above, by the non-glycosylated endogenous peptide concentration obtained above.

In various embodiments, a process for concentration determination can improve normalization results when combined with the other processes described here. Please see X. Experimental Results and FIGS. 7A and 7B.

VII. Exemplary Normalization Methods

VII.A. Normalized Abundance Methods

In various embodiments, any of the methods described herein can be performed on any system capable of carrying out the describes individual steps of the method. A non-limiting example of a system is described in FIG. 3 along with associated description provided herein.

In various embodiments, the below steps can be stored on a non-transitory computer-readable medium including computer instructions that, when executed by a computer, cause the computer to perform the below method for determining a concentration of a target glycopeptide analyte.

Referring to FIG. 5, a method of determining a concentration of a target glycopeptide analyte in a sample is described according to some embodiments.

Step 502 comprises measuring a non-glycosylated endogenous peptide (NGEP) abundance value for an NGEP in a sample in accordance with various embodiments.

Step 504 comprises determining a corrected NGEP abundance value for the transition using an external standard in accordance with various embodiments.

Step 506 comprises measuring an internal standard abundance for an internal standard having a known internal standard concentration in accordance with various embodiments.

Step 508 comprises determining a NGEP concentration value as a function of the corrected NGEP abundance value, the known internal standard concentration, and the internal standard abundance in accordance with various embodiments.

Step 510 comprises determining a normalized abundance value of a target glycopeptide analyte as a function of a first measured abundance of the target glycopeptide analyte and a second measured abundance of a non-glycosylated peptide on the same protein as the target glycoprotein analyte in accordance with various embodiments.

Step 512 comprises determining a target glycopeptide analyte concentration as a function of the NGEP concentration value and the normalized abundance value in accordance with various embodiments.

In various embodiments, an NGEP concentration value comprises a ratio of the corrected NGEP abundance value and the internal standard abundance. In various embodiments, an NGEP concentration value can be a product of the ratio and the known internal standard concentration.

In various embodiments, a normalized abundance value can be determined when one or two glycans are present at a target glycosylation site on the protein.

In various embodiments, a target glycopeptide analyte concentration can be a product of an NGEP concentration value and a normalized abundance value.

In various embodiments, a normalized abundance value can be the quotient of a first measured abundance and a second measured abundance.

In various embodiments, the abundance for the NGEP, the internal standard abundance, and the measured abundance of the target glycopeptide can be measured in a sample run using mass spectrometry.

VII.B. Site Occupancy Methods

In various embodiments, any of the methods described herein can be performed on any system capable of carrying out the describes individual steps of the method. A non-limiting example of a system is described in FIG. 3 along with associated description provided herein.

In various embodiments, the below steps can be stored on a non-transitory computer-readable medium including computer instructions that, when executed by a computer, cause the computer to perform the below method for determining a concentration of a target glycopeptide analyte in a sample.

Referring to FIG. 6, a method of determining a concentration of a target glycopeptide analyte in a sample is described in accordance with various embodiments.

Step 602 comprises obtaining a non-glycosylated endogenous peptide (NGEP) abundance value for a NGEP in a sample in accordance with various embodiments.

Step 604 comprises determining a corrected NGEP abundance value for the transition using an external standard in accordance with various embodiments.

Step 606 comprises measuring an internal standard abundance for an internal standard having a known internal standard concentration in accordance with various embodiments.

Step 608 comprises determining a NGEP concentration value as a function of the corrected NGEP abundance value, the known internal standard concentration, and the internal standard abundance in accordance with various embodiments.

Step 610 comprises determining a site occupancy value of a target glycopeptide analyte as a function of a measured target abundance of the target glycopeptide analyte at a given site, and a measured total abundance of all glycopeptides at the same site in accordance with various embodiments.

Step 612 comprises determining a target glycopeptide analyte concentration as a function of the NGEP concentration value and the normalized abundance value in accordance with various embodiments.

In various embodiments, an NGEP concentration value comprises a ratio of the corrected NGEP abundance value and the internal standard abundance. In various embodiments, an NGEP concentration value can be a product of the ratio and the known internal standard concentration.

In various embodiments, a normalized abundance value can be determined when one or two glycans are present at a target glycosylation site on the protein.

In various embodiments, a target glycopeptide analyte concentration can be a product of an NGEP concentration value and a normalized abundance value.

In various embodiments, a normalized abundance value can be the quotient of a first measured abundance and a second measured abundance.

In various embodiments, the abundance for the NGEP, the internal standard abundance, and the measured abundance of the target glycopeptide can be measured in a sample run using mass spectrometry.

VII.C. Exemplary Methods of Determining Glycopeptide Concentration

In various embodiments, any of the methods described herein can be performed on any system capable of carrying out the describes individual steps of the method. A non-limiting example of a system is described in FIG. 3 along with associated description provided herein.

In various embodiments, the below steps can be stored on a non-transitory computer-readable medium including computer instructions that, when executed by a computer, cause the computer to perform the below method for determining a concentration of a target glycopeptide analyte in a sample.

Referring to FIG. 9, a method of determining a concentration of a target glycopeptide analyte in a sample is described in accordance with various embodiments.

Step 902 comprises receiving raw abundance data for a sample from a mass spectrometry system, the raw abundance data comprising a raw external standard abundance for an external standard in the sample, a raw internal standard abundance for an internal standard that has a known concentration in the sample, a raw glycopeptide abundance for a glycopeptide structure in the sample, a raw non-glycosylated peptide abundance for a non-glycosylated peptide structure in the sample, the non-glycosylated peptide structure being derived from a same glycoprotein as the glycopeptide structure. In various embodiments, a single run can analyze a sample comprising an external standard, an internal standard, and a glycopeptide analyte. As such, abundance values (e.g. abundance or raw abundance) for external standard, internal standard, and target glycopeptide analyte can be determined by mass spectrometry in the same run.

Step 904 comprises computing corrected abundance data using a difference between the raw external standard abundance and a reference abundance for the external standard. In some embodiments, computing the corrected abundance data comprises computing a corrected abundance for the non-glycosylated peptide structure.

Step 906 comprises generating normalized concentration data for the sample using the corrected abundance data, the raw internal standard abundance, the known concentration of the internal standard, the raw glycopeptide abundance, and the raw non-glycosylated peptide abundance. In some embodiments, generating comprises computing a non-glycosylated peptide concentration using the corrected abundance and the raw internal standard abundance. In some embodiments, generating comprises computing a normalized abundance for the glycopeptide structure using the raw glycopeptide abundance for the glycopeptide structure and the raw non-glycosylated peptide abundance for the non-glycosylated peptide structure. In some embodiments, generating comprises computing a normalized concentration for the glycopeptide structure using the normalized abundance for the glycopeptide structure and the non-glycosylated peptide concentration for the non-glycosylated peptide structure, wherein the concentration data includes the normalized concentration for the glycopeptide structure.

In various embodiments, the normalized concentration data can be normalized to account for variances across a plurality of experiments run on the mass spectrometry system.

In various embodiments, the normalized concentration data can be normalized to account for variances across a plurality of experiments run on different mass spectrometry systems.

In various embodiments, the normalized concentration data can be normalized to account for variances across a plurality of experiments run in different laboratories.

In various embodiments, the normalized concentration data can be normalized to account for variances when analyzing a plurality of samples across at least one of a plurality of experiments, a plurality of laboratories, or a plurality of different mass spectrometry systems.

Step 908 comprises analyzing the normalized concentration data using a model system to generate an output for a subject. In various embodiments, the output comprises a treatment output. In various embodiments, the output comprises a diagnosis output.

VIII. Exemplary Sample Preparation and LC-MS
Run Order Methods

Predictive capabilities of predictive algorithms can be influenced by sample preparation and LC-MS run order methods. The methods and systems for data normalization described herein can be influenced by the individual constituents (e.g., a patient sample and one or more standards) of the run samples and the position of the run sample on a run order.

FIG. 13 illustrates a flowchart of an exemplary method for preparing samples for a LC-MS sample run and normalizing abundance data of a plurality of sample runs 1300.

Step 1302 includes preparing run samples for a plurality of sample runs for LC-MS analysis. In many methods, preparing run samples can include generating a first set of run samples. In many methods, preparing run samples can include generating a second set of run samples.

Each of the first set of run samples can include an external standard. In many embodiments, the external standard can originate from an external standard source. In some embodiments, the external standard source can include a serum. In various embodiments, an external standard can include an NGEP. In various embodiments, a source for an external standard can match a source for a biological sample. In various embodiments, a source includes plasma. In some embodiments, a source includes whole blood. In some embodiments, a source includes tissue. A non-limiting example may include pooled plasma digests being used as external standards when biological/patient samples to be characterized include plasma samples.

In various embodiments, a pooled standard originating from a serum source (e.g., sigma serum or pooled plasma serum), being used as an external standard in the method of normalization described herein, does not have a known concentration. (e.g., a constituent analyte prior to the LC/MS). In various embodiments, the concentration of the external standard may be unknown prior to LC-MS analysis. In various embodiments, the concentration of the pooled standard may be unknown prior to LC-MS analysis.

In various embodiments, a type of an external standard can match a type of a biological sample. In various embodiments, a type can include a peptide structure or sequence of a peptide structure (e.g., a standard and a glycopeptide analyte may have a sequence similarity greater than 99%, 95%, 90%, or 85%). In various embodiments, a type can include a peptide structure including a glycosylation site. In various embodiments, a type can include an m/z ratio (e.g., a standard and a glycopeptide analyte having an m/z ratio similarity greater than 80%, 85%, 90%, 95%, or 99%). In various embodiments, a type can include an abundance (e.g., a standard and a glycopeptide analyte having an abundance similarity greater than 80%, 85%, 90%, 95%, or 99%).

In certain embodiments, a type of biological sample used for an external standard may be matched to the source or type of biological sample being charactered in a patient sample, the abundances generated from peptide structures being normalized (e.g. pooled plasma digests to plasma samples, pooled serum digests to serum samples, pooled whole blood digests to whole blood samples).

Each of the second set can include at least two target glycopeptide analytes and an internal standard.

The step of preparing can further comprise enzymatically digesting glycoprotein structures of the various run samples to generate the external standards, the internal standards, and the at least two target glycopeptide analytes of the run samples. Exemplary processing protocols including digestion are discussed through the present description.

Step 1304 includes combining at least two run samples of the first set to create a pooled standard.

Step 1306 includes analyzing each run sample according to a run order, wherein the run order specifies a relative order of analysis for the run samples of the sample run. A run sample of the first set can occupy an adjacent position in the run order to a run sample of the second set, in protocols. In many protocols, a run sample of the first set can occupy a position before all of the run samples of the second set. In additional and other protocols, a run sample of the first set can occupy a position after all of the run samples of the second set.

In some protocols, the run order comprises analyzing one run sample of the first set at least every five positions in the run order. In other protocols, the run order comprises analyzing one run sample of the first set at least every ten positions in the run order. In still other protocols, the run order comprises analyzing one run sample of the first set at least every fifteen positions in the run order.

For most protocols, the run order comprises analyzing one sample of the first set followed by a range of between two and twenty-nine run samples of the second set. In many protocols, the run order comprises analyzing one sample of the first set followed by a range of between four and fourteen run samples of the second set.

Additionally, protocols can include runs orders that specify analyzing at least one run sample comprising BSA before all the run samples of the first and second sets have been analyzed. Still other protocols can include analyzing at least one run sample comprising BSA after all the run samples of the first and second sets have been analyzed.

Protocols can include analyzing at least one blank run sample prior to analyzing a run sample of the first or the second set in a run order. Protocols for run order can include analyzing a blank run sample one position before analyzing a sample of the first set in the run order. In various embodiments, blank run samples can include water.

Step 1308 includes normalizing the raw abundance data of the plurality of sample runs by using the pooled standard of each sample run as a reference.

Some processes include normalizing raw abundance data generated from each of the plurality of target glycopeptide analytes of the same run sample using the internal standards. Internal standard can comprise a non-glycosylated endogenous peptide (NGEP). In some embodiments, each target glycopeptide analyte can have a corresponding internal standard for a reference. In some cases, an internal standard can comprise a surrogate.

IX. Exemplary Sample Processing System

Figure 14:
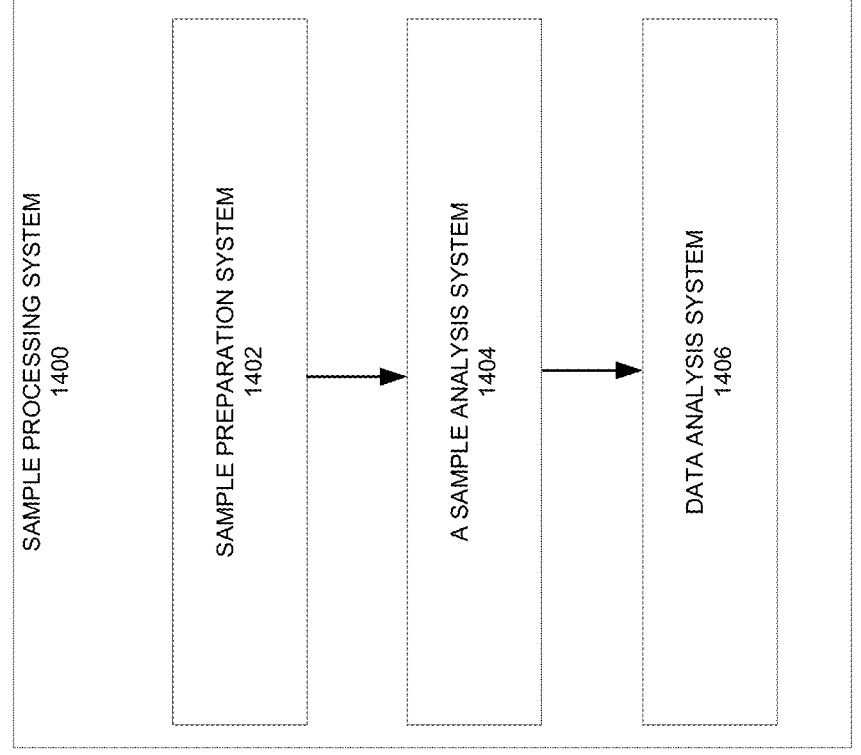
FIG. 14 illustrates an exemplary sample processing system for processing patient sample into normalized abundance.

FIG. 14 illustrates an exemplary sample processing system 1400 for processing patient sample into normalized abundance. A sample processing system 1400 can include a sample preparation system 1402, a sample analysis system 1404, and a data analysis system 1406. The sample processing systems described herein can comprise hardware and instructions for carrying out the processes described in FIGS. 1, 2A, 2B, 5, 6, 9, and 13.

A sample preparation system 1402 can include a fluidic instrument for processing glycoproteins into glycopeptide analytes in accordance with the various embodiments described herein. The fluidic instrument can include one or more pipettes. The sample preparation system 1402 can include partitions for storing run samples prior to analysis, for mixing, and for other sample predation steps (e.g., digestion). Non-limiting examples of partitions can include vials and wells (e.g., wells of a 96-well plate).

The sample preparation system 1402 can generate a first set of run samples, each of the first set including an external standard. In various embodiment, an external standard can include an NGEP. In various embodiments, a source for an external standard can match a source for a biological sample. In various embodiments, a source includes plasma. In some embodiments, a source includes whole blood. In some embodiments, a source includes tissue. A non-limiting example may include pooled plasma digests being used as external standards when biological/patient samples to be characterized include plasma samples. In various embodiments, a pooled standard originating from a serum source (e.g., sigma serum or pooled plasma serum), being used as an external standard in the method of normalization described herein, does not have a known concentration. (e.g., a constituent analyte prior to the LC/MS). In various embodiments, the concentration of the external standard may be unknown prior to LC-MS analysis. In various embodiments, the concentration of the pooled standard may be unknown prior to LC-MS analysis.

In various embodiments, a type of an external standard can match a type of a biological sample. In various embodiments, a type can include a peptide structure or sequence of a peptide structure (e.g., a standard and a glycopeptide analyte may have a sequence similarity greater than 99%, 95%, 90%, or 85%). In various embodiments, a type can include a peptide structure including a glycosylation site. In various embodiments, a type can include an m/z ratio (e.g., a standard and a glycopeptide analyte having an m/z ratio similarity greater than 80%, 85%, 90%, 95%, or 99%). In various embodiments, a type can include an abundance (e.g., a standard and a glycopeptide analyte having an abundance similarity greater than 80%, 85%, 90%, 95%, or 99%).

In certain embodiments, a type of biological sample used for an external standard may be matched to the source or type of biological sample being charactered in a patient sample, the abundances generated from peptide structures being normalized (e.g. pooled plasma digests to plasma samples, pooled serum digests to serum samples, pooled whole blood digests to whole blood samples).

The sample preparation system 1402 can generate a second set of run samples, each of the second set including at least two target glycopeptide analytes and an internal standard, The sample preparation system 1402 can combine at least two run samples of the first set to create a pooled standard. The combining step can occur after enzymatic digestion in some embodiments. In other embodiments, the combining step can occur before enzymatic digestion. The step of preparing can further comprise enzymatically digesting glycoprotein structures of the run samples to generate the external standards, the internal standards, and the at least two target glycopeptide analytes of the run samples. Non-limiting examples of preparation processes that can be carried out on the sample preparation system 1402 are illustrated in FIG. 2A and described in Section IV.A. Sample Preparation and Processing.

The sample analysis system 1404 can include a LC-MS instrument for analyzing glycopeptide analytes. A process comprising analyzing each run sample according to a run order can be carried out on the LC-MS, wherein the run order can be stored on a data store in electronical communication with the LC-MS instrument and specifies a relative order of analysis for the run samples of the sample run. Non-limiting examples of sample analysis that can be carried out on the sample analysis system 1404 are illustrated in FIG. 2B and described in Section IV.B. Peptide Structure Identification and Processing.

In many processes a run sample of the first set occupies an adjacent position in the run order to a run sample of the second set. In many processes a run sample of the first set occupies a position in the run order before all of the run samples of the second set. In many processes a run sample of the first set occupies a position in the run order in the after all of the run samples of the second set. In some processes, the run order comprises analyzing one run sample of the first set at least every five positions in the run order. In more processes, the run order comprises analyzing one run sample of the first set at least every ten positions in the run order. In many processes, the run order comprises analyzing one run sample of the first set at least every fifteen positions in the run order. The run order can comprise analyzing one sample of the first set followed by a range of between two and twenty-nine run samples of the second set. The run order can comprise analyzing one sample of the first set followed by a range of between four and fourteen run samples of the second set. In some systems the process can include analyzing at least one run sample comprising BSA before all the run samples of the first and second sets have been analyzed. Some processes of the system include analyzing at least one run sample comprising BSA after all the run samples of the first and second sets have been analyzed. Some processes of the system include analyzing at least one blank run sample prior to analyzing a run sample of the first or the second set. Some processes of the system include analyzing a blank run sample one position before analyzing a sample of the first set in the run order.

The data analysis system 1406 can further include a normalization module. Normalization 312 shown in FIG. 3 can be an example of the normalization module. The exemplary normalization methods described herein can be processes using the data normalization module (see Section VII. Exemplary Normalization Methods). The process further comprises normalizing raw abundance data generated from each of the plurality of target glycopeptide analytes of the same run sample using the internal standards.

In many systems the external standard comprises a non-glycosylated endogenous peptide (NGEP). In many systems, each target glycopeptide analyte can have a corresponding internal standard for a reference. At least some of the internal standards can be surrogates. In many systems, serum comprises the external standard and can be an external standard source.

X. Experimental Results

X.A. Normalization Methods

The experimental results described below demonstrate the differential accuracy achieved using the systems and methods described herein versus alternatives.

Figure 7A:
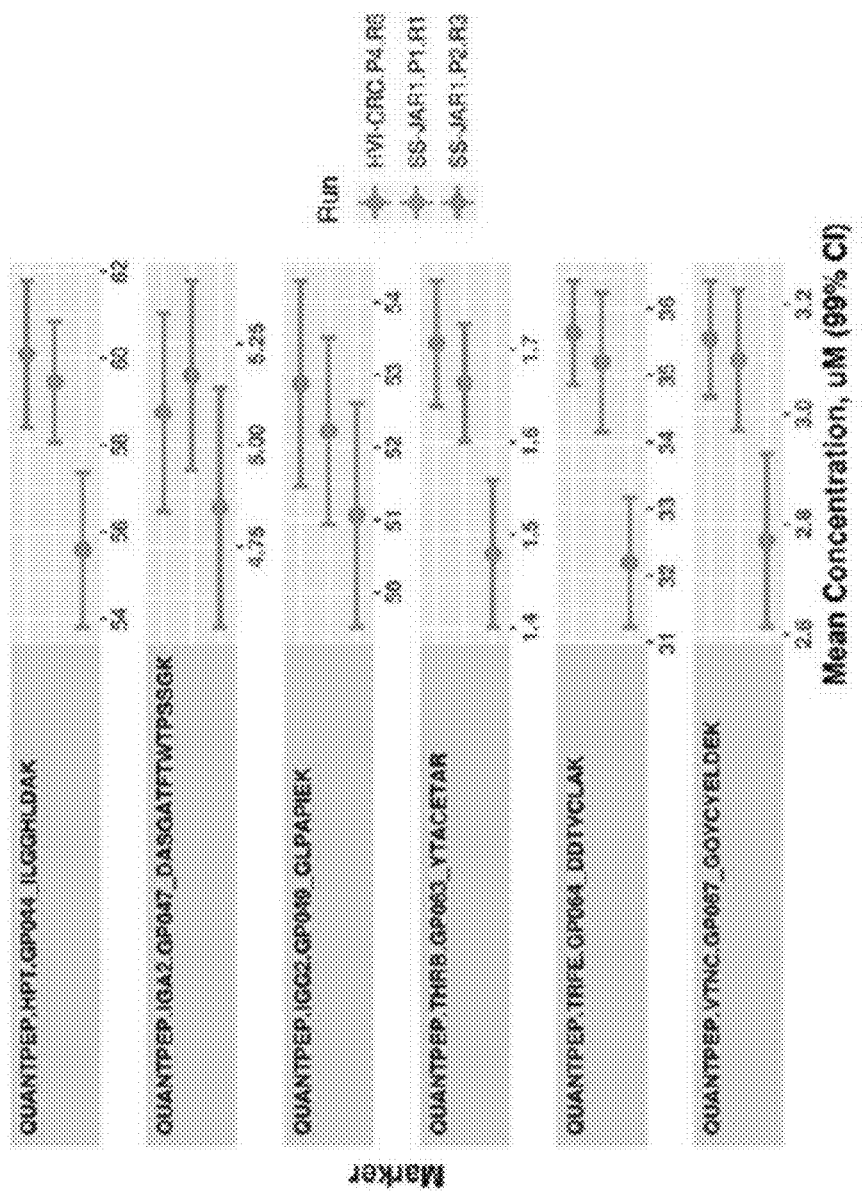
FIG. 7A illustrates experimental data showing a normalization result that does not employ combined external standards combined with internal standard and relativistic approaches. For each marker, the top horizontal line is SS-JAR1.P2.R3, the middle horizontal line is SS-JAR1.P1.R1, and the bottom horizontal line is HVI-CRC.P4.R6.

Referring to FIG. 7A, mean concentrations with 99% confidence intervals for six markers are presented. The mean concentrations for the six markers were determined using the following method.

In determining a mean concentration FIG. 7A uses a process that employs no external standard-based abundance correction (see VI.A. Normalize Data Using External Standard), and this leads to misaligned results in peptide concentration across three separate runs, as observed in the difference between the HVI-CRC run and the SS-JAR1 run.

Figure 7B:
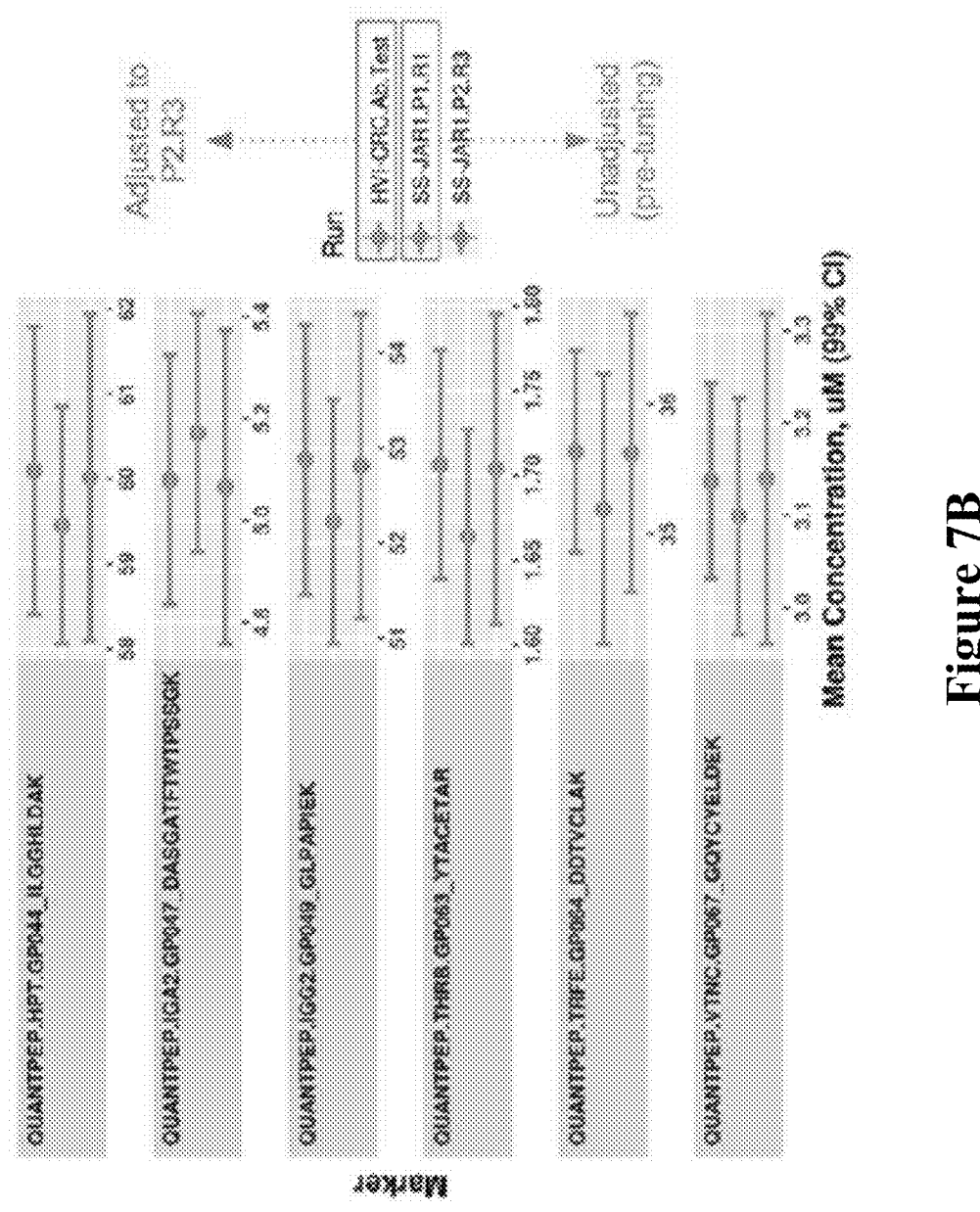
FIG. 7B illustrates experimental data showing a normalization resulting by adding an additional step of abundance correction via external standard to the combined approaches in 7A. For each marker, the top horizontal line is SS-JAR1.P2.R3, the middle horizontal line is SS-JAR1.P1.R1, and the bottom horizontal line is HVI-CRC.Ab.Test.

Referring to FIG. 7B, mean concentrations for the six marks are presented when completing an abundance correction step (e.g. Normalize Data Using External Standard) prior to the process used in generating the data shown in FIG. 7A, namely, for every new run, on a per-marker basis, abundance data was corrected for differences in ionization and digestion efficiency by multiplying by the quotient of Sigma Serum means of the new run and some reference. Corrected_Patient_Abundance=Patient_Abundance*(ReferenceRun_Mean-Sigma Serum_Abundance/ NewRun_Mean_Sigma Serum_Abundance). This results in aligned peptide concentrations, which allows for comparing aligned approximate glycopeptide concentrations.

FIG. 7A compared to FIG. 7B demonstrate that without a specified order of steps (e.g. Normalize Data Using External Standard step occurring first and Concentration Determination occurring last), peptide level data will not align. As such, various embodiments described herein benefit in ordering the Normalize Data Using External Standard step first and Concentration Determination last.

Figure 10A:
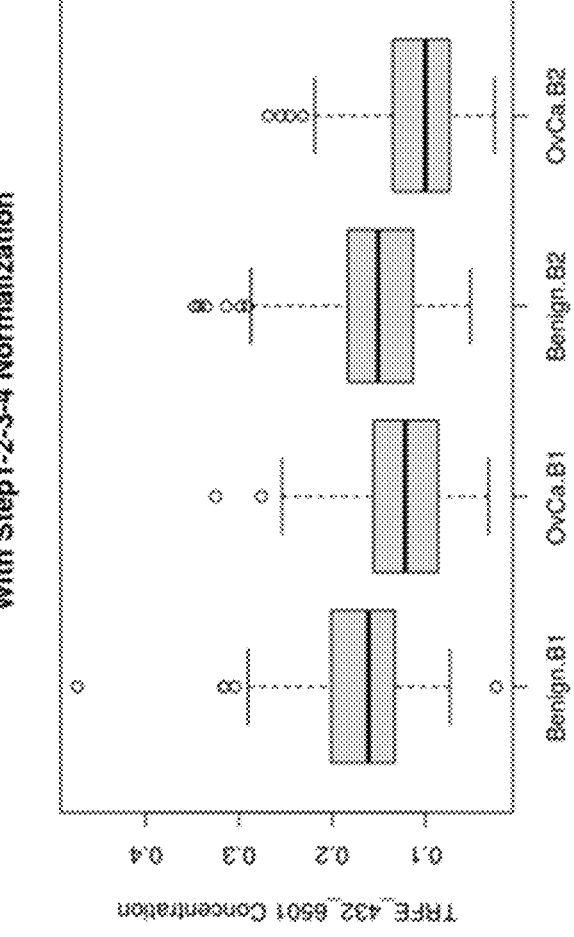
FIG. 10A illustrates experimental data where process Normalize Data Using External Standard occurs prior to processes Normalize Data Using Internal Standard and Site Occupancy Abundance and process Concentration Determination occurs last.
Figure 10B:
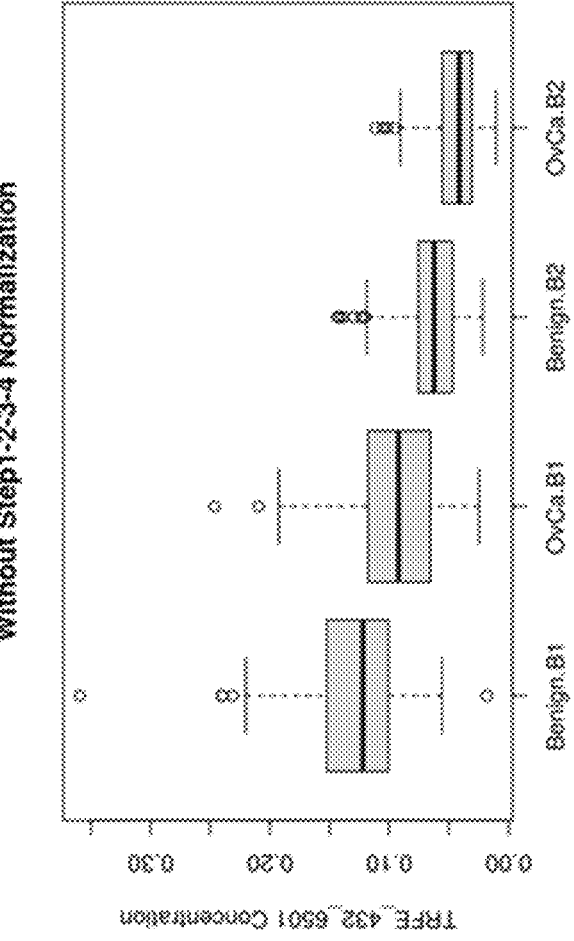
FIG. 10B illustrates the same experimental data from FIG. 10A where process Normalize Data Using External Standard does not occur.

FIG. 10A and FIG. 10B illustrate a comparison of independent ovarian cancer and benign cohorts in batch 1 ("B1") and batch 2 ("B2"). FIG. 10A represents a single glycopeptide concentration calculated via site occupancy and the Normalize Data Using External Standard step occurring first and Concentration Determination occurring last, resulting in similar disease distributions.

FIG. 10B displays the same marker and patients without using the abundance correction to an external standard step (e.g. the Normalize Data Using External Standard step), resulting in batch 2 values that do not align with batch 1. As such, the data in FIG. 10B cannot be effectively compared whereas the data in FIG. 10A can be effectively compared and used in conjunction with predictive models.

Figure 11A:
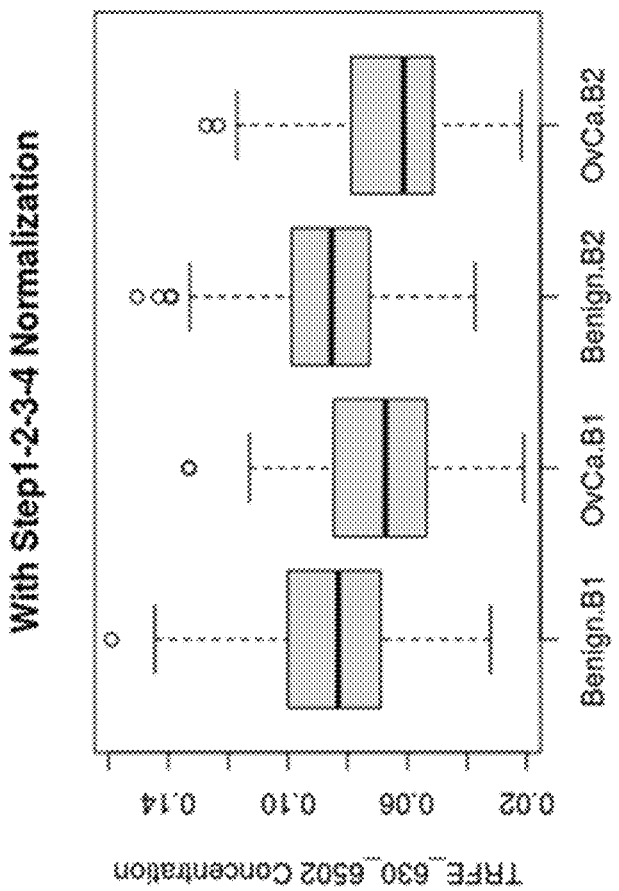
FIG. 11A illustrates experimental data where process Normalize Data Using External Standard occurs prior to processes Normalize Data Using Internal Standard and Relative Abundance and process Concentration Determination occurs last.
Figure 11B:
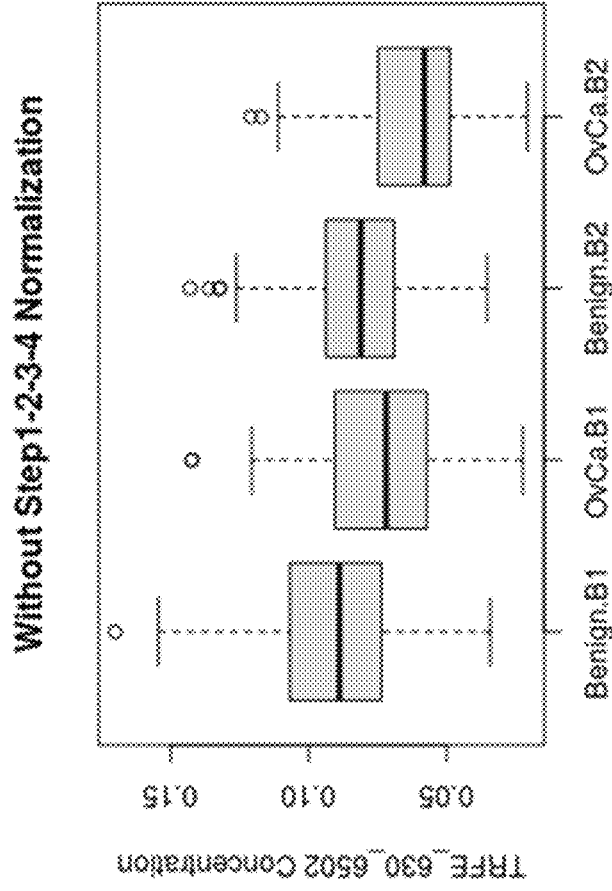
FIG. 11B illustrates the same experimental data from FIG. 11A where process Normalize Data Using External Standard does not occur.

FIG. 11A and FIG. 11B illustrate a comparison of independent ovarian cancer and benign cohorts in batch 1 ("B1") and batch 2 ("B2"). FIG. 10A represents a single glycopeptide concentration calculated via relative abundance and the Normalize Data Using External Standard step occurring first and Concentration Determination occurring last, resulting in similar disease distributions.

FIG. 11B displays the same marker and patients without using the abundance correction to an external standard step (e.g. the Normalize Data Using External Standard step), resulting in batch 2 values that do not align with batch 1. As such, the data in FIG. 11B cannot be effectively compared whereas the data in FIG. 11A can be effectively compared and used in conjunction with predictive models.

Figure 12A:
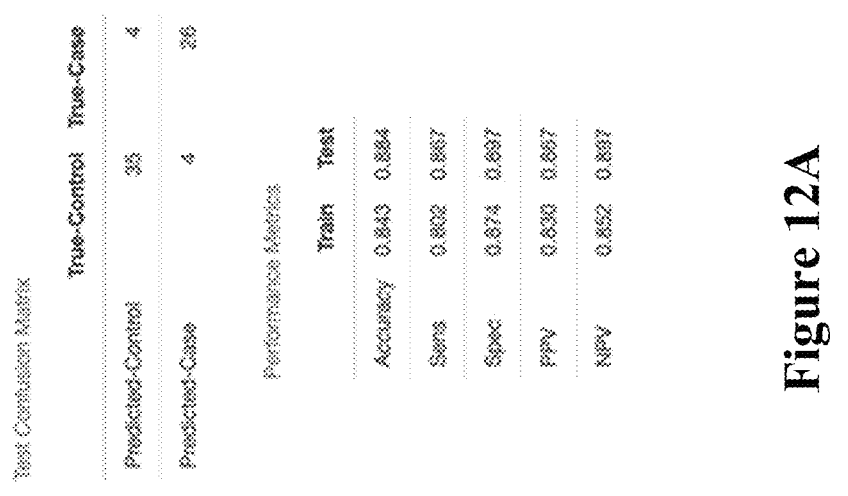

FIG. 12A and FIG. 12B illustrate confusion matrices resulting in applying a trained ovarian cancer model to an independent test set. FIG. 12A represents a model where concentration was calculated using a Normalize Data Using External Standard step first and Concentration Determination last. FIG. 12B represents a model where concentration was calculated omitting the Normalize Data Using External Standard step. Overall, the predictive accuracy seen in FIG. 12A was determined to be 0.884 and the predictive accuracy seen in FIG. 12B was determined to be 0.71. As such, completing Normalize Data Using External Standard step first, following by completing the Normalize Data Using Internal Standard and Relativistic Normalization steps and finally the Concentration Determination was shown to increase predictive accuracy by 0.174.

X.B. Sample Preparation and Processing

Figure 15:
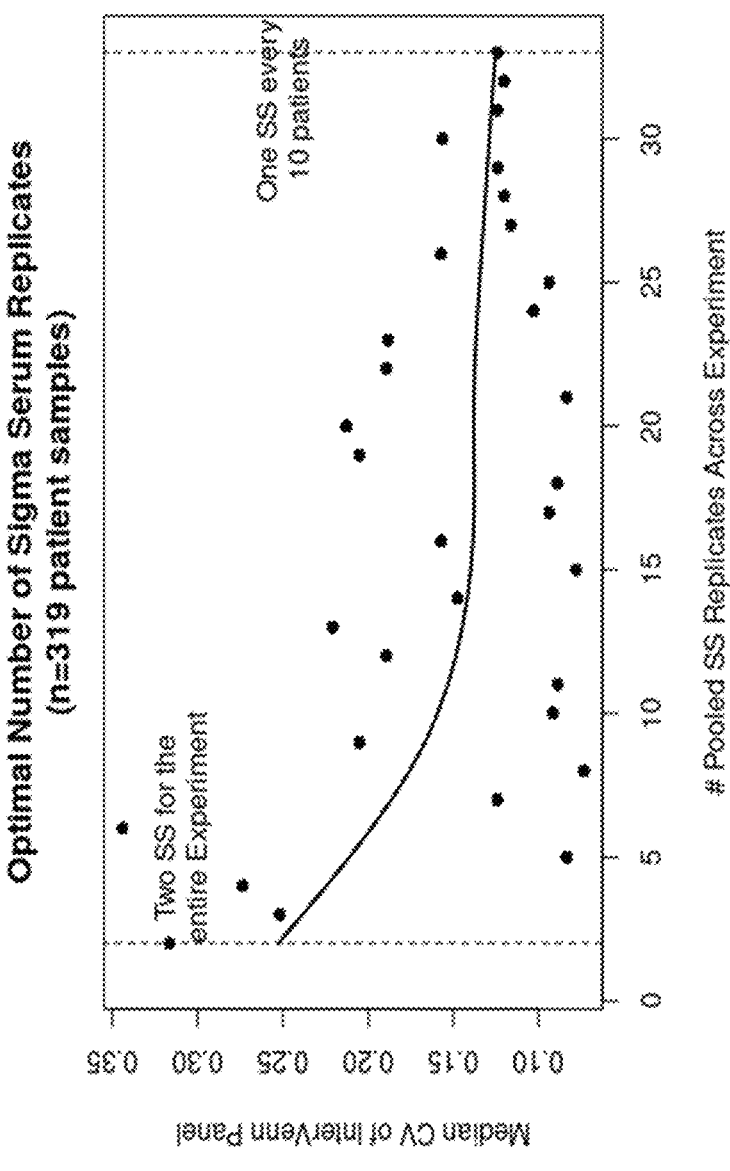
FIG. 15 illustrates experimental results for data including coefficient of variation for pooled replicates.

FIG. 15 illustrates experimental results for data including coefficient of variation for pooled replicates. The data demonstrates that including too few external standards (e.g., sigma serum (SS) replicates) in an experiment may not allow accurate estimations for a coefficient of variation (CV)

of biomarkers (e.g., glycopeptide analytes) undergoing mass spectrometry analysis. The median CV of all biomarkers is plotted for each possibility from n=2 SS for the entire experiment (left line) up to one SS every 10 patient samples (right, with n=33 SS for n=319 patients). As the frequency of SS replicates increases, the variance around this median CV decreases to a low amount as the estimation approaches the true median CV (0.124).

FIG. 16 illustrates an experimental run order for a set of run samples. Run samples include blanks, BSA, system buffer, target glycopeptide analytes, internal standards, and external standards. In the run order pooled standard, "SS-JAR1-SysSuit," is run every $10^{th}$ position and a blank in the position just prior in a run order. A sample position coordinate system can be used for robot fluidic instrument mediated sample preparation. The run order was generated using a run order algorithm. The algorithm was written into a script that automatically generated a run sequence based on patient sample data. The algorithm took a list of patient samples with external sample IDs and their corresponding internal sample IDs, then randomized the samples and put a SS digest at the beginning and after every 10 randomized patient samples and assigned them sample preparation numbers starting from #1, and then the samples were randomized again and put into the designed run sequence pattern with interspersed blanks and SS pool runs.

FIG. 17 illustrates a layout for a 96-well plate including run sample partition locations. Non-limiting constituents of run samples can include blanks, BSA, system buffer, target glycopeptide analytes, internal standards, and external standards. "ss" followed by a number identify locations of external standards, "SS" identifies pooled standards, the other markers indicate other run samples (e.g., run samples including target glycopeptide analytes and/or internal standards).

XI. Additional Considerations

Any headers and/or subheaders between sections and subsections of this document are included solely for the purpose of improving readability and do not imply that features cannot be combined across sections and subsection. Accordingly, sections and subsections do not describe separate embodiments.

While the present teachings are described in conjunction with various embodiments, it is not intended that the present teachings be limited to such embodiments. On the contrary, the present teachings encompass various alternatives, modifications, and equivalents, as will be appreciated by those of skill in the art. The present description provides preferred exemplary embodiments, and is not intended to limit the scope, applicability or configuration of the disclosure. Rather, the present description of the preferred exemplary embodiments will provide those skilled in the art with an enabling description for implementing various embodiments.

It is understood that various changes may be made in the function and arrangement of elements without departing from the spirit and scope as set forth in the appended claims. Thus, such modifications and variations are considered to be within the scope set forth in the appended claims. Further, the terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed.

In describing the various embodiments, the specification may have presented a method and/or process as a particular sequence of steps. However, to the extent that the method or process does not rely on the particular order of steps set forth herein, the method or process should not be limited to the particular sequence of steps described, and one skilled in the art can readily appreciate that the sequences may be varied and still remain within the spirit and scope of the various embodiments.

Some embodiments of the present disclosure include a system including one or more data processors. In some embodiments, the system includes a non-transitory computer readable storage medium containing instructions which, when executed on the one or more data processors, cause the one or more data processors to perform part or all of one or more methods and/or part or all of one or more processes disclosed herein. Some embodiments of the present disclosure include a computer-program product tangibly embodied in a non-transitory machine-readable storage medium, including instructions configured to cause one or more data processors to perform part or all of one or more methods and/or part or all of one or more processes disclosed herein.

Specific details are given in the present description to provide an understanding of the embodiments. However, it is understood that the embodiments may be practiced without these specific details. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

XII. Recitation of Embodiments

Embodiment 1: A method of determining a concentration of a target glycopeptide analyte in a sample, the method comprising: measuring an abundance for a non-glycosylated endogenous peptide (NGEP) of a sample; determining a corrected NGEP abundance for the NGEP using an external standard; measuring an internal standard abundance for an internal standard having a known internal standard concentration; determining an NGEP concentration for the NGEP as a function of the corrected NGEP abundance, the known internal standard concentration, and the internal standard abundance; determining a normalized abundance of a target glycopeptide analyte of the sample as a function of a measured abundance of the target glycopeptide analyte and the measured abundance of the NGEP on the same protein as the target glycoprotein analyte; and determining a target glycopeptide analyte concentration as a function of the NGEP concentration and the normalized abundance.

Embodiment 2: The method of embodiment 1, further comprising analyzing the target glycopeptide analyte concentration to generate a treatment for a subject.

Embodiment 3: The method of embodiments 1 or 2, further comprising analyzing the target glycopeptide analyte concentration to generate a diagnosis for a subject.

Embodiment 4: The method of any one of embodiments 1-3, wherein the NGEP concentration comprises a ratio of the corrected NGEP abundance and the internal standard abundance.

Embodiment 5: The method of embodiment 4, wherein the NGEP concentration is a product of the ratio and the known internal standard concentration.

Embodiment 6: The method of any one of embodiments 1-5, wherein the normalized abundance is determined when one or two glycans are identified at a target glycosylation site on the protein.

Embodiment 7: The method of any one of embodiments 1-6, wherein the target glycopeptide analyte concentration is a product of the NGEP concentration and the normalized abundance.

Embodiment 8: The method of any one of embodiments 1-7, wherein the normalized abundance is the quotient of the first measured abundance and the second measured abundance Embodiment 9: The method of any one of embodiments 1-8, wherein the abundance for the NGEP, the internal standard abundance, and the measured abundance of the target glycopeptide are measured in a sample run using mass spectrometry.

Embodiment 10: A non-transitory computer-readable medium storing computer instructions that, when executed by a computer, cause the computer to perform a method for determining a concentration of a target glycopeptide analyte in a sample, the method comprising: measuring an abundance for a non-glycosylated endogenous peptide (NGEP) of a sample; determining a corrected NGEP abundance for the NGEP using an external standard; measuring an internal standard abundance for an internal standard having a known internal standard concentration; determining an NGEP concentration as a function of the corrected NGEP abundance, the known internal standard concentration, and the internal standard abundance; determining a normalized abundance of a target glycopeptide analyte of the sample as a function of a measured abundance of the target glycopeptide analyte and the measured abundance of the NGEP on the same protein as the target glycoprotein analyte; and determining a target glycopeptide analyte concentration as a function of the NGEP concentration and the normalized abundance.

Embodiment 11: The method of embodiment 10, further comprising analyzing the target glycopeptide analyte concentration to generate a treatment for a subject.

Embodiment 12: The method of embodiments 10 or 11, further comprising analyzing the target glycopeptide analyte concentration to generate a diagnosis for a subject.

Embodiment 13: The method of any one of embodiments 10-12, wherein the NGEP concentration comprises a ratio of the corrected NGEP abundance and the internal standard abundance.

Embodiment 14: The method of embodiment 13, wherein the NGEP concentration is a product of the ratio and the known internal standard concentration.

Embodiment 15: The method of any one of embodiments 10-14, wherein the normalized abundance is determined when one or two glycans are identified at a target glycosylation site on the protein.

Embodiment 16: The method of any one of embodiments 10-15, wherein the target glycopeptide analyte concentration is a product of the NGEP concentration and the normalized abundance.

Embodiment 17: The method of any one of embodiments 10-16, wherein the normalized abundance is the quotient of the first measured abundance and the second measured abundance.

Embodiment 18: The method of any one of embodiments 10-17, wherein the abundance for the NGEP, the internal standard abundance, and the measured abundance of the target glycopeptide are measured in a sample run using mass spectrometry.

Embodiment 19: A method of determining a concentration of a target glycopeptide analyte in a sample, the method comprising: measuring an abundance for a non-glycosylated endogenous peptide (NGEP) of a sample; determining a corrected NGEP abundance for the NGEP using an external standard; measuring an internal standard abundance for an internal standard having a known internal standard concentration; determining a NGEP concentration as a function of the corrected NGEP abundance, the known internal standard concentration, and the internal standard abundance; determining a site occupancy of a target glycopeptide analyte of the sample as a function of a measured target abundance of the target glycopeptide analyte at a given site, and a measured total abundance of all glycopeptides quantified at the same site; and determining a target glycopeptide analyte concentration as a function of the NGEP concentration and the normalized abundance.

Embodiment 20: The method of embodiment 19, further comprising analyzing the target glycopeptide analyte concentration to generate a treatment for a subject.

Embodiment 21: The method of embodiments 19 or 20, further comprising analyzing the target glycopeptide analyte concentration to generate a diagnosis for a subject.

Embodiment 22: The method of any one of embodiments 19-21, wherein the NGEP concentration comprises a ratio of the corrected NGEP abundance and the internal standard abundance Embodiment 23: The method of embodiment 22, wherein the NGEP concentration is a product of the ratio and the known internal standard concentration.

Embodiment 24: The method of any one of embodiments 19-23, wherein the site occupancy is determined when three or more glycans are identified at the given site.

Embodiment 25: The method of any one of embodiments 19-24, wherein the target glycopeptide analyte concentration is a product of the NGEP concentration and the normalized abundance.

Embodiment 26: The method of any one of embodiments 19-25, wherein the site occupancy is the quotient of the measured target abundance and the measured total abundance.

Embodiment 27: The method of any one of embodiments 19-26, wherein the abundance for the NGEP, the internal standard abundance, and the measured abundance of the target glycopeptide are measured in a sample run using mass spectrometry.

Embodiment 28: A non-transitory computer-readable medium storing computer instructions that, when executed by a computer, cause the computer to perform a method for determining a concentration of a target glycopeptide analyte in a sample, the method comprising: measuring an abundance for a non-glycosylated endogenous peptide (NGEP) of a sample; determining a corrected NGEP abundance for the NGEP using an external standard; measuring an internal standard abundance for an internal standard having a known internal standard concentration; determining a NGEP concentration as a function of the corrected NGEP abundance, the known internal standard concentration, and the internal standard abundance; determining a site occupancy of a target glycopeptide analyte of the sample as a function of a measured target abundance of the target glycopeptide analyte at a given site, and a measured total abundance of all glycopeptides at the same site; and determining a target glycopeptide analyte concentration as a function of the NGEP concentration and the normalized abundance.

Embodiment 29: The method of embodiment 28, further comprising analyzing the target glycopeptide analyte concentration to generate a treatment for a subject.

Embodiment 30: The method of embodiments 28 or 29, further comprising analyzing the target glycopeptide analyte concentration to generate a diagnosis for a subject.

Embodiment 31: The method of any one of embodiments 28-30, wherein the NGEP concentration comprises a ratio of the corrected NGEP abundance and the internal standard abundance Embodiment 32: The method of embodiment 31, wherein the NGEP concentration is a product of the ratio and the known internal standard concentration.

Embodiment 33: The method of any one of embodiments 28-32, wherein the site occupancy is determined when three or more glycans are identified at the given site.

Embodiment 34: The method of any one of embodiments 28-33, wherein the target glycopeptide analyte concentration is a product of the NGEP concentration and the normalized abundance.

Embodiment 35: The method of any one of embodiments 28-34, wherein the site occupancy is the quotient of the measured target abundance and the measured total abundance.

Embodiment 36: The method of any one of embodiments 28-35, wherein the abundance for the NGEP, the internal standard abundance, and the measured abundance of the target glycopeptide are measured in a sample run using mass spectrometry.

Embodiment 37: A method for preparing samples for a liquid chromatography/mass spectrometry (LC-MS) sample run and normalizing abundance data of a plurality of sample runs, the method comprising: preparing run samples for the plurality of sample runs for LC-MS analysis, the preparing comprising: generating a first set of run samples, each of the first set of run samples including an external standard; and generating a second set of run samples, each of the second set of run samples including at least two target glycopeptide analytes and an internal standard; combining at least two run samples of the first set of run samples to create a pooled standard; analyzing each run sample according to a run order, wherein the run order specifies a relative order of analysis for the run samples of the sample run; and normalizing the raw abundance data of the plurality of sample runs using the pooled standard of each sample run as a reference.

Embodiment 38: The method of embodiment 37, wherein a first run sample of the first set of run samples occupies an adjacent position in the run order to a second run sample of the second set of run samples.

Embodiment 39: The method of embodiment 37, wherein a run sample of the first set of run samples occupies a position in the run order before all of the run samples of the second set of run samples.

Embodiment 40: The method of embodiment 37, wherein a run sample of the first set of run samples occupies a position in the run order after all of the run samples of the second set of run samples.

Embodiment 41: The method of embodiment 37, wherein a run sample of the first set of run samples occupies one position for at least every five positions in the run order.

Embodiment 42: The method of embodiment 37, wherein a run sample of the first set of run samples occupies one position for at least every ten positions in the run order.

Embodiment 43: The method of embodiment 37, wherein the run order comprises a single run sample of the first set of run samples positioned at least every fifteen positions in the run order.

Embodiment 44: The method of embodiment 37, wherein the run order comprises a single run sample of the first set of run samples followed by a range of between two and twenty-nine run samples of the second set of run samples.

Embodiment 45: The method of embodiment 37, wherein the run order comprises a single run sample of the first set of run samples followed by a range of between four and fourteen run samples of the second set of run samples.

Embodiment 46: The method of any one of embodiments 37-45, further comprising: positioning at least one run sample comprising BSA before all the run samples of the first set of run samples and the second set of run samples in the run order.

Embodiment 47: The method of any one of embodiments 37-46, further comprising: positioning at least one run sample comprising BSA after all the run samples of the first set of run samples and the second set of run samples in the run order.

Embodiment 48: The method of any one of the embodiments 37-47, further comprising: positioning at least one blank run sample before a run sample of the first set of run samples or the second set of run samples in the run order.

Embodiment 49: The method of any one of the embodiments 37-48, further comprising: positioning a blank run sample one position before a run sample of the first set of run samples in the run order.

Embodiment 50: The method of any one of embodiments 37-49, wherein the step of preparing further comprises: enzymatically digesting glycoprotein structures of the run samples to generate the external standard of each run sample of the first set of run samples and the internal standard and the at least two target glycopeptide analytes of each run sample of the second set of run samples.

Embodiment 51: The method of embodiment 50, further comprising: normalizing raw abundance data generated from each of the at least two target glycopeptide analytes of a same run sample of the second set of run samples using the internal standards.

Embodiment 52: The method of any one of embodiments 37-51, wherein the external standard comprises a non-glycosylated endogenous peptide (NGEP).

Embodiment 53: The method of any one of embodiments 37-52, wherein each of the at least two target glycopeptide analytes has a corresponding internal standard for a reference.

Embodiment 54: The method of any one of embodiments 37-53, wherein the internal standard of at least one run sample of the second set of run samples is a surrogate.

Embodiment 55: The method of any one of embodiments 37-54, wherein a source of the external standard includes serum.

Embodiment 56: The method of any one of embodiments 37-55, wherein an external standard of the first set of run samples includes at least one pooled plasma digest when a run sample in the second set of runs samples includes a patient plasma sample.

Embodiment 57: The method of embodiment 56, wherein the patient plasma sample includes a target analyte.

Embodiment 58: The method of any one of embodiments 37-57, wherein the concentration of the external standard is unknown prior to analyzing.

Embodiment 59: The method of any one of embodiments 37-58, wherein the concentration of the pooled standard is unknown prior to analyzing.

Embodiment 60: A sample processing system for carrying out a process for preparing samples for a liquid chromatography/mass spectrometry (LC-MS) sample run and normalizing abundance data of a plurality of sample runs, the sample processing system comprising: a sample preparation system, including a fluidic instrument, for performing a process comprising: generating a first set of run samples, each of the first set including an external standard; generating a second set of run samples, each of the second set including at least two target glycopeptide analytes and an internal standard; and combining at least two run samples of the first set to create a pooled standard; a sample analysis system, including a LC-MS instrument, for analyzing glycopeptide analytes, the process comprising analyzing each run sample according to a run order, wherein the run order is stored on a data store in electronical communication with the LC-MS instrument and specifies a relative order of analysis for the run samples of the sample run; and a data analysis system, including a normalization module of a peptide structure analyzer, for normalizing raw abundance data of the plurality of sample runs using the pooled standard of each sample run as a common reference.

Embodiment 61: The system of embodiment 60, wherein a first run sample of the first set of run samples occupies an adjacent position in the run order to a second run sample of the second set of run samples.

Embodiment 62: The system of embodiment 60, wherein a run sample of the first set of run samples occupies a position before all of the run samples of the second set of run samples in the run order.

Embodiment 63: The system of embodiment 60, wherein a run sample of the first set of run samples occupies a position after all of the run samples of the second set of run samples in the run order.

Embodiment 64: The system of embodiment 60, wherein the run order comprises a single run sample of the first set of run samples positioned at least every five positions in the run order.

Embodiment 65: The system of embodiment 60, wherein the run order comprises a single run sample of the first set of run samples positioned at least every ten positions in the run order.

Embodiment 66: The system of embodiment 60, wherein the run order comprises a single run sample of the first set of run samples positioned at least every fifteen positions in the run order.

Embodiment 67: The system of embodiment 60, wherein the run order comprises a single run sample of the first set of run samples followed by a range of between two and twenty-nine run samples of the second set.

Embodiment 68: The system of embodiment 60, wherein the run order comprises a single run sample of the first set of run samples followed by a range of between four and fourteen run samples of the second set of run samples.

Embodiment 69: The system of any one of embodiments 60-68, wherein at least one run sample comprising BSA is positioned before all the run samples of the first set of run samples and the second set of run samples in the run order.

Embodiment 70: The system of any one of embodiments 60-69, wherein at least one run sample comprising BSA is positioned after all the run samples of the first set of run samples and the second set of run samples in the run order.

Embodiment 71: The system of any one of embodiments 60-70, wherein at least one blank run sample is positioned before a run sample of the first set of run samples or the second set of run samples in the run order.

Embodiment 72: The system of any one of embodiments 60-71, wherein a blank run sample is positioned one position before a run sample of the first set of run samples in the run order.

Embodiment 73: The system of any one of embodiments 60-72, wherein the process performed using the sample preparation system further comprises enzymatically digesting glycoprotein structures of the run samples to generate the external standard of each run sample of the first set of run samples and the internal standard and the at least two target glycopeptide analytes of each run sample of the second set of run.

Embodiment 74: The system of any one of embodiments 60-73, wherein the data analysis system is configured to normalize the raw abundance data generated from each of the at least two target glycopeptide analytes of a same run sample using the internal standard.

Embodiment 75: The system of any one of embodiments 60-74, wherein the external standard comprises a non-glycosylated endogenous peptide (NGEP).

Embodiment 76: The system of any one of embodiments 60-75, wherein the external standard comprises a non-glycosylated endogenous peptide (NGEP).

Embodiment 77: The system of any one of embodiments 60-76, wherein each of the at least two target glycopeptide analytes has a corresponding internal standard for a reference.

Embodiment 78: The system of any one of embodiments 60-77, wherein the internal standard of at least one run sample of the second set of run samples is a surrogate.

Embodiment 79: The system of any one of embodiments 60-78, wherein a source of the external standard includes serum.

Embodiment 80: The system of any one of embodiments 60-79, wherein an external standard of the first set of run samples includes at least one pooled plasma digest when a run sample in the second set of runs samples includes a patient plasma sample.

Embodiment 81: The system of embodiment 80, wherein the patient plasma sample includes a target analyte.

Embodiment 82: The system of any one of embodiments 60-81, wherein the concentration of the external standard is unknown prior to analyzing.

Embodiment 83: The system of any one of embodiments 60-82, wherein the concentration of the pooled standard is unknown prior to analyzing.

Embodiment 84: The method of any one of embodiments 1-9 and 19-27, further comprising a method for preparing samples for a LC-MS sample run and normalizing abundance data of a plurality of sample runs, of any one of embodiments 37-59.

Embodiment 85: The method of any one of embodiments 10-18 and 28-36, further comprising a method for preparing samples for a LC-MS sample run and normalizing abundance data of a plurality of sample runs, of any one of embodiments 37-59.

What is claimed is:

1. A method of determining a concentration of a target glycopeptide analyte in a sample, the method comprising:
  measuring an abundance for a non-glycosylated endogenous peptide (NGEP) of a sample;
  determining a corrected NGEP abundance for the NGEP using an external standard;
  measuring an internal standard abundance for an internal standard having a known internal standard concentration;
  determining an NGEP concentration for the NGEP as a function of the corrected NGEP abundance, the known internal standard concentration, and the internal standard abundance;
  determining a normalized abundance of a target glycopeptide analyte of the sample as a function of a measured abundance of the target glycopeptide analyte and the measured abundance of the NGEP on the same protein as the target glycoprotein analyte; and
  determining a target glycopeptide analyte concentration as a function of the NGEP concentration and the normalized abundance.

2. The method of claim 1, further comprising analyzing the target glycopeptide analyte concentration to generate a treatment for a subject.

3. The method of claim 1, further comprising analyzing the target glycopeptide analyte concentration to generate a diagnosis for a subject.

4. The method of claim 1, wherein the NGEP concentration comprises a ratio of the corrected NGEP abundance and the internal standard abundance.

5. The method of claim 4, wherein the NGEP concentration is a product of the ratio and the known internal standard concentration.

6. The method of claim 1, wherein the normalized abundance is determined when one or two glycans are identified at a target glycosylation site on the protein.

7. The method of claim 1, wherein the target glycopeptide analyte concentration is a product of the NGEP concentration and the normalized abundance.

8. The method of claim 1, wherein the normalized abundance is a quotient of a first measured abundance of the target glycopeptide analyte and a second measured abundance of a non-glycosylated peptide on the same protein as the target glycoprotein analyte.

9. The method of claim 1, wherein the abundance for the NGEP, the internal standard abundance, and the measured abundance of the target glycopeptide are measured in a sample run using mass spectrometry.

* * * * *